United States Patent
Zaragoza Sánchez et al.

(10) Patent No.: US 9,644,019 B2
(45) Date of Patent: May 9, 2017

(54) COMPOUNDS FOR TREATING CARDIAC DAMAGE AFTER ISCHAEMIA/REPERFUSION

(75) Inventors: Carlos Zaragoza Sánchez, Madrid (ES); Mónica Gómez Parrizas, Madrid (ES); Begoña Lavín Plaza, Madrid (ES); Carlos Tarín Cerezo, Madrid (ES)

(73) Assignees: Carlos Zaragoza Sánchez, Madrid (ES); Carlos Tarín Cerezo, Madrid (ES)

(*) Notice: Subject to any disclaimer, the term of this patent is extended or adjusted under 35 U.S.C. 154(b) by 272 days.

(21) Appl. No.: 14/110,805

(22) PCT Filed: Dec. 1, 2011

(86) PCT No.: PCT/ES2011/070832
§ 371 (c)(1),
(2), (4) Date: Feb. 6, 2014

(87) PCT Pub. No.: WO2012/072850
PCT Pub. Date: Jun. 7, 2012

(65) Prior Publication Data
US 2014/0148396 A1 May 29, 2014

(30) Foreign Application Priority Data

Dec. 2, 2010 (ES) .................................. 201031794

(51) Int. Cl.
| | |
|---|---|
| C07K 14/705 | (2006.01) |
| G01N 33/543 | (2006.01) |
| C07K 16/28 | (2006.01) |
| A61K 47/48 | (2006.01) |
| A61K 38/00 | (2006.01) |
| A61K 39/00 | (2006.01) |
| B82Y 5/00 | (2011.01) |

(52) U.S. Cl.
CPC .. C07K 14/70503 (2013.01); A61K 47/48861 (2013.01); C07K 16/2803 (2013.01); G01N 33/54346 (2013.01); A61K 38/00 (2013.01); A61K 2039/505 (2013.01); B82Y 5/00 (2013.01); C07K 2317/76 (2013.01)

(58) Field of Classification Search
None
See application file for complete search history.

(56) References Cited

U.S. PATENT DOCUMENTS 8,618,264 B2 12/2013 Cunningham et al.
2005/0026841 A1* 2/2005 Chen et al. ..................... 514/15

FOREIGN PATENT DOCUMENTS

WO 2007028053 A2 3/2007
WO 2010036460 A2 4/2010

OTHER PUBLICATIONS

Waiker et al (J Am Soc Nephrol. Jan. 2012; 23(1): 13-21).*
Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000,10:398-400).*
Guido et al (Curr Med Chem. 2008;15(1):37-46).*
Clark et al (J. Med. Chem., 2014, 57 (12), pp. 5023-5038).*
Takasaki (Methods Mol Biol. 2013;942:17-55).*
Martinez-Sanchez et al (Biology 2013, 2, 189-205).*
Warzocha et al (Leukemia and Lymphoma, Val. 24. pp. 267-281).*
Tarin, Carlos, et al.; "The extracellular matrix metaloproteinase inducer EMMPRIN is a target of nitric oxide in myocardial ischemia/reperfusion." Free Radical Biology & Medicine, 2011, pp. 387-395, vol. 51.
Seizer, Peter, et al.; "Disrupting the EMPPRIN (CD147)-Cyclophilin A Interaction Reduces Infarct Size and Preserves Systolic Function After Myocardial Ischemia and Reperfusion." Arteriosclerosis, Thrombosis, and Vascular Biology, 2011, pp. 1377-1386, vol. 31.
Seizer, P., et al.; "Targeting the funtion of EMMPRIN (CD147) reduces infarct size and preserves systolic function after ischaemia and reperfusion." Clinical Research in Cardiology: Official Journal of the German Cardiac Society, 2010, p. 1, vol 99. Abstract Only.
Biswas, Chitra, et al.; "The Human Tumor Cell-derived Collagenase Stimulatory Factor (Renamed EMMPRIN) Is a Member of the Immunoglobulin Superfamily." Cancer Research, 1995, pp. 434-439, vol. 55.
Hanna, M., et al.; "A novel form of the membrane protein CD147 that contains an extra ig-like domain and interacts homophilically." BMC Biochemistry, 2003, pp. 1-9, vol. 4.
Seko, Yoshinori, et al.; "Hypoxia followed by reoxygenation induces secretion of cyclophilin A from cultured rat cardiac myocytes." Biochemical and Biophysical Research Communications, 2004, pp. 162-168, vol. 317.
Romanic, Anne M., et al.; "Mycardial protection from ischemia/reperfusion injury by targeted deletion of matrix metalloproteinase-9." Cardiovascular Research, 2002, pp. 549-558, vol. 54.
Castejón, B., et al.; "Nitric Oxide: Front cardiopretection ischemia/reperfusion by inhibition of CD147." La Revista del CNEM, 2009, pp. 1-8.
Sun, Hai-Yan, et al.; "Propofol improves cardiac functional recovery after ischemia-reperfusion by upregulating nitric oxide synthase activity in the isolated rat hearts." Chinese Midical Journal, 2009, pp. 3048-3054, vol. 122.

(Continued)

*Primary Examiner* — Brian J Gangle
*Assistant Examiner* — Andrea McCollum
(74) *Attorney, Agent, or Firm* — Tristan A. Fuierer; Moore & Van Allen, PLLC

(57) ABSTRACT

The present invention relates to the use of an Extracellular Matrix Metalloproteinase Inducer (EMMPRIN) inhibitor for preventing and/or treating cardiac damage arising after an ischemic process followed by reperfusion. The authors of the present invention have observed that EMMPRIN expression increases in subjects who have suffered ischemia/reperfusion, ascertaining that an EMMPRIN inhibitor is capable of reducing the cardiac damage caused after ischemia followed by reperfusion, both in vitro and in vivo.

11 Claims, 14 Drawing Sheets

(56) References Cited

OTHER PUBLICATIONS

Kann, Shinichi, et al.; "Altenuation of Mycardial Ischemia/Reperfusion Injury by Superinduction of Inducible Nitric Oxide Synthase." Circulation, 2000, pp. 2742-2748, vol. 101.

Ohman, E. Magnus, et al.; "Cardiac Troponin T Levels for Risk Stratification in Acute Myocardial Ischemia." The New England Journal of Medicine, 1996, pp. 1333-1341, vol. 335.

Zhang, Feng, et al.; "Monocarboxylate Transporter Expression in the Spontaneous Hypertensive Rat: Effect of Stroke." Journal of Neuroscience Research, 2005, pp. 139-145, vol. 79.

International Search Report dated Jun. 12, 2012.

\* cited by examiner

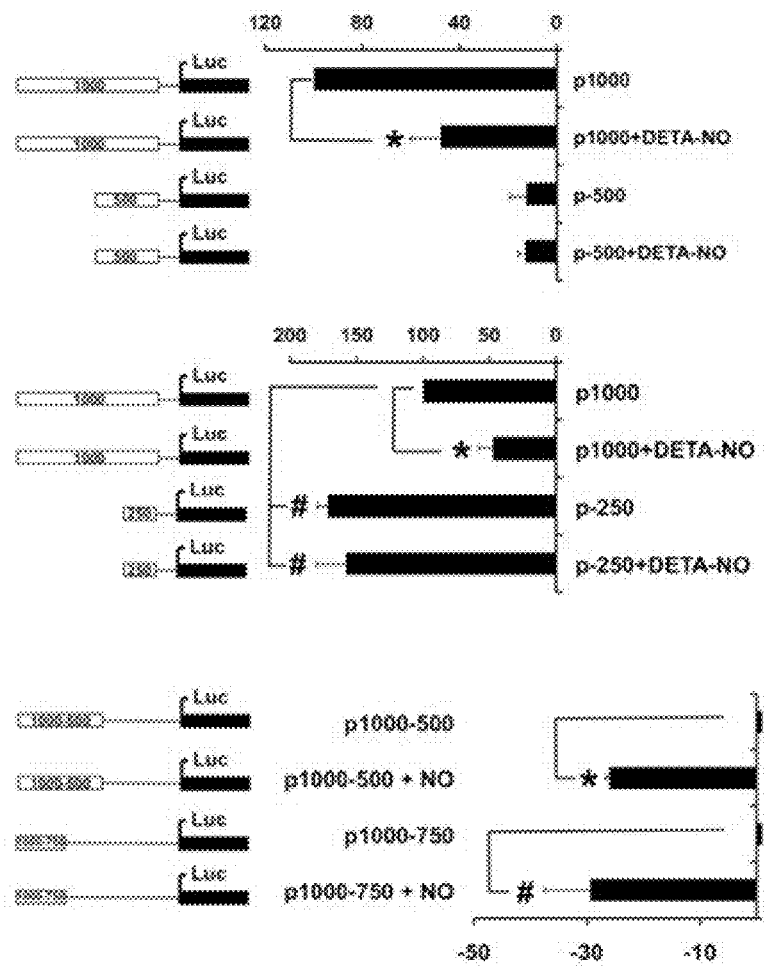
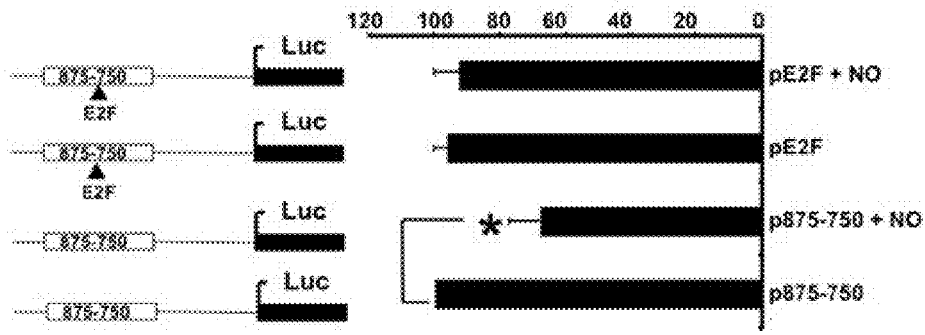
FIGURE 5

US 9,644,019 B2

COMPOUNDS FOR TREATING CARDIAC DAMAGE AFTER ISCHAEMIA/REPERFUSION

CROSS-REFERENCE TO RELATED APPLICATIONS

This application is filed under the provisions of 35 U.S.C. §371 and claims the priority of International Patent Application No. PCT/ES2011/070832 filed on 1 Dec. 2011 entitled "COMPOUNDS FOR TREATING CARDIAC DAMAGE AFTER ISCHAEMIA/REPERFUSION" in the name of Carlos ZARAGOZA SÁANCHEZ, et al., which claims priority to Spanish Patent Application No. P201031794, filed on 2 Dec. 2010, both of which are hereby incorporated by reference herein in their entirety.

FIELD OF THE INVENTION

The invention relates to the use of an Extracellular Matrix Metalloproteinase Inducer inhibitor for preventing and/or treating cardiac damage arising after an ischemic process followed by reperfusion.

BACKGROUND OF THE INVENTION

Ischemic heart disease or myocardial ischemia is characterized by a significant drop of the blood supply to the heart muscle, the necessary oxygen and nutrient levels thereby decreasing. The most common cause of myocardial ischemia is due to occlusion of the coronary arteries as the result of an atherosclerotic process, the risk of which increases with age, in smokers, in subjects with hypercholesterolemia, diabetes and hypertension, and it is more common in male subjects.

Coronary occlusion results in the onset of ischemic necrosis or myocardial infarct, the incidence of which is directly related to the degree of oxygen and nutrient deprivation in the tissue. In the case of transient ischemia, subsequent reperfusion of the myocardium is directly associated with a spread of the myocardial necrosis referred to as lethal reperfusion injury.

Under hypoxia, cardiomyocytes are dependent on glycolysis as energy metabolism. The transport of lactic acid produced as a glycolysis byproduct is necessary for maintaining the cell viability and is carried out through lactate transporters called MCT-1 and MCT-4, the association of the latter with the protein called CD147 (also called Basigin or EMMPRIN (Extracellular Matrix Metalloproteinase Inducer)) having been described (Halestrap et al. 1999. Biochem J; 343: 281-299). Both MCT and EMMPRIN are overexpressed in ischemia in neuronal and heart cells (Zhang et al. 2005; J. Neurosc. Res. 79: 139-145). In the case of MCTs, overexpression is related to a protective effect against lactate build up. In the case of EMMPRIN, the effect is still unknown due to its interaction with other proteins, the process being extremely complex.

There are compounds described in the literature that have the capacity to reduce damage caused by cardiac ischemia. The use of nitrates (Pfister M et al. Heart 80 (4): 365-9), beta-blocking compounds (O'Rourke S T. Am J Pharm Educ, 2007; 71 (5): 95) (acebutolol or metoprolol) and agents that reduce hypertension has been described. Likewise, nitric oxide could also be used as a cardioprotective agent, because its efficacy has been verified through its impact in different mechanisms (West M B et al. Circulation. 2008; 118:1970-8. Lin J, et al., Circulation 2009; 120:245-54), including the use of substances such as propofol, which increase the production thereof in ischemia followed by reperfusion (Sun Hai-yan et al. Chin. Med. J 2009; 122: 3048-54). However, NO has a dual effect due to the fact of its significant involvement in oxidative stress associated with cardiac damage taking place during myocardial infarct (Liu Y H et al. American journal of physiology 2005; 289:H2616-2623), and to the fact that a significant increase of its production associated with an increase of cardiac damage in humans has been detected (Mungrue I N et al. J Clin Invest 2002; 109:735-743), whereas the use of NOS inhibitors such as L-NAME have been evaluated in various studies with at least promising, although not conclusive, results (Cotter G et al. European heart journal 2003; 24:1287-1295), suggesting that the effect of NO on the heart may be related to the time in which and the dose at which this factor occurs.

In relation to the effect of NO as a cardioprotective agent, it is important to stress the effect of the so-called ischemic pre-conditioning, a phenomenon that consists of the occurrence of repeated ischemia processes of a short duration, as a result of which the heart is capable of successfully tolerating the following prolonged ischemic processes after reperfusion. Among the different factors inducing the pre-conditioning process, NO is one of them, its efficacy in the cardioprotective process having been demonstrated (Xuan Y T et al. Circulation. 2007; 116: 535-44; West M B, et al. Circulation. 2008; 118:1970-8), and although various candidates associated with NO production in the process have been described, it is necessary to continue progressing in the in-depth knowledge of the cardioprotection exerted by this factor.

Despite the fact that compounds have been described for preventing or treating the symptoms associated with ischemia/reperfusion, there is a need to develop new compounds for reducing cardiac damage after ischemia followed by reperfusion that are more efficient than those described in the state of the art.

BRIEF DESCRIPTION OF THE INVENTION

In one aspect, the invention relates to the use of an EMMPRIN inhibitor or of an inhibitor of a functionally equivalent EMMPRIN variant for preparing a medicinal product for preventing and/or treating cardiac damage arising after ischemia followed by reperfusion.

BRIEF DESCRIPTION OF THE DRAWINGS

FIG. 5 describes that transcriptional repression of NO on the EMMPRIN promoter is mediated by E2F factor in cardiomyocytes. (A) Effect of NO on EMMPRIN promoter transcriptional activity in cardiomyocytes transiently transfected with pEMMPRIN-WT (p1000), and with serial deletions of the promoter. Upper area: p1000 and p500 transcriptional activity (n=3, mean±SD *p<0.05 vs p1000). Central area: p1000 and p250 transcriptional activity (n=3, mean±SD *p<0.05 p1000+DETA-NO vs p1000. #p<0.05 vs p1000). Lower area: p1000-500 and p1000-750 transcriptional activity, construct containing the 250 distal bps of 1000 (n=3, mean±SD. *p<0.05 vs p1000-500. # p<0.05 vs p1000-750). (B) p875-750 transcriptional activity and p875-750 variant transcriptional activity in which point mutation of the E2F transcription factor binding site has been induced (n=3, mean±SD. *p<0.05 p875-750 vs p875-750+NO).

DETAILED DESCRIPTION OF THE INVENTION

Figure 1:
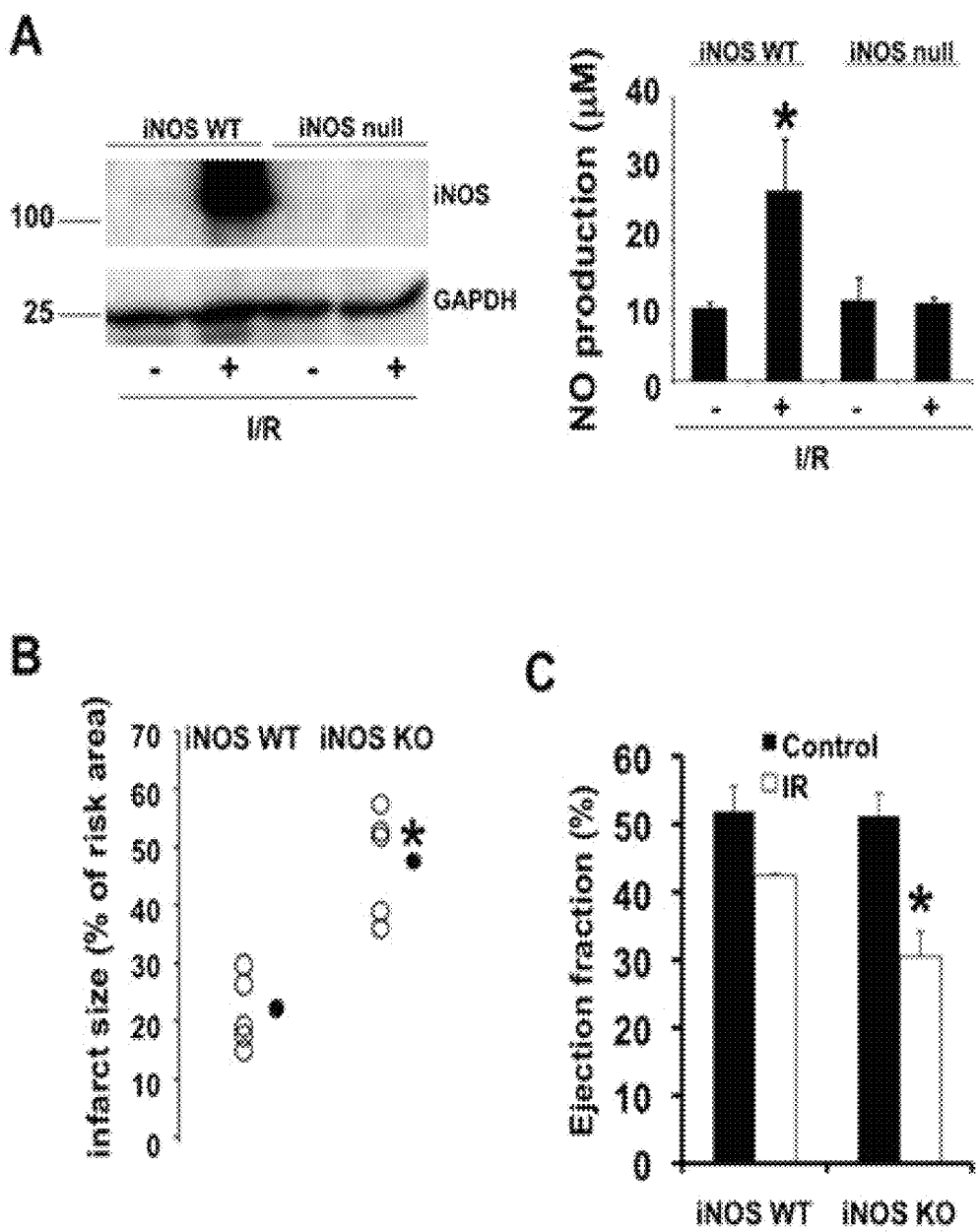
FIG. 1 describes that the absence of NO increases myocardial damage during ischemia/reperfusion. (A) left: iNOS WT and iNOS knockout mice were subjected to 30 minutes of coronary ischemia, followed by 24 hours of reperfusion, then evaluating the iNOS levels (and GAPDH levels as load control) in a Western-blot. (A) right: NO production, (n=6, mice in triplicate, mean±SD; p<0.05 iNOS WT+ vs iNOS WT−). (B) Infarct size (n=6, mice in triplicate, p<0.05 iNOS WT vs iNOS knockout). (C) Ejection fraction values (n=6, mice in triplicate, mean±SD; p<0.05 iNOS WT IR vs iNOS knockout IR). IR: Ischemia followed by reperfusion.

The authors of the present invention have observed that EMMPRIN expression increases in subjects who have suffered ischemia/reperfusion, ascertaining that an EMMPRIN inhibitor is capable of reducing cardiac damage caused after ischemia followed by reperfusion. Therefore, as is illustrated in Example 6, where ischemia/reperfusion is reproduced in mice, the administration of anti-EMMPRIN antibodies caused a significant reduction of EMMPRIN and recovery of cardiac function (ejection fraction) until reaching levels similar to the controls.

Up until now, the presence of the EMMPRIN protein had never been associated with events related to the reperfusion of the coronary arteries. Other researchers have detected how ischemia, but not reperfusion, of the coronary arteries involves the occurrence of acute myocardial infarct, detecting increases in EMMPRIN expression and in the expression of EMMPRIN-associated MMPs in infiltrated monocytes (Schmidt R et al. Circulation 2006; 113:834-841). Nevertheless, these documents do not mention the possible role of EMMPRIN in ischemia/reperfusion or its role as a target for reducing or preventing lesions caused by ischemia/reperfusion.

Therefore in a first aspect, the invention relates to the use of an EMMPRIN inhibitor or of an inhibitor of a functionally equivalent variant of said protein, for preparing a medicinal product for preventing and/or treating cardiac damage arising after ischemia followed by reperfusion. Alternatively, the invention relates to an EMMPRIN inhibitor or to an inhibitor of a functionally equivalent EMMPRIN variant for use in preventing and/or treating cardiac damage arising after ischemia followed by reperfusion. Alternatively, the invention relates to a method for preventing and/or treating cardiac damage arising after ischemia followed by reperfusion in a subject, comprising the administration to said subject of an EMMPRIN inhibitor or of an inhibitor of a functionally equivalent EMMPRIN variant.

As it is used herein, the term "EMMPRIN" refers to an Extracellular Matrix Metalloproteinase Inducer, which is a member of the immunoglobulin (Ig) superfamily and a product of the bsg gene. The names "Basigin", "EMMPRIN" and "CD147" will be used herein interchangeably. The EMMPRIN protein, isoform the accession number of which in the NCBI human protein database is NP-940991 (SEQ ID NO:1) (version from Jul. 18, 2010) is a highly glycosylated (with three conserved N-glycosylation sites that are glycosylated variably), 269 amino acid-long transmembrane polypeptide. EMMPRIN is a pleiotropic molecule that plays an important role in fetal development, retinal function and in T-cell maturation. It has been proven to act as a cell surface receptor for cyclophilins. It is expressed in tissue remodeling areas, such as tumors, endometrium, placenta, skin and regions showing angiogenesis (Iacono et al. 2007. Exp Mol. Path 83:283-295). On the other hand, EMMPRIN stimulates VEGF production and is capable of inducing the expression of several collagenases or matrix metalloproteinases (MMPs), such as MMP1, MMP2, MMP3, MMP9 and MMP11. With respect to the structure of EMMPRIN, the protein contains two C2 type extracellular Ig domains, a transmembrane domain and a cytoplasmic domain (Miyauchi T et al. J Biochem. 1991; 110:770-4). Most inter-species differences are in the extracellular domains. It seems that the N-terminal Ig domain is required for stimulating MMP production by EMMPRIN (Biswas C et al. Cancer Res 1995; 55:434-9) and that it is necessary and sufficient for oligomerization, probably through hydrophobic interactions (Tang W et al. Mol Biol Cell 2004; 15:4043-50).

The invention also contemplates the use of inhibitors of functionally equivalent variants of said proteins. "Functionally equivalent variant" is understood as all those polypeptides derived from the EMMPRIN sequence by means of modification, insertion and/or deletion of one or more amino acids, provided that the function of the EMMPRIN protein is substantially maintained. Specifically, the functionally equivalent EMMPRIN variant conserves at least one function related to the induction of the different MMPs (Schmidt R et al. mentioned ad supra) or to the capacity to promote cardiac damage in ischemia after reperfusion by increasing the concentration thereof (Castejón B. Revista CNEM, n°1. 2009).

Functionally equivalent EMMPRIN variants include those showing at least 25%, at least 40%, at least 60%, at least 70%, at least 80%, at least 90%, at least 95%, at least 96%, at least 97%, at least 98% or at least 99% sequence identity with respect to the EMMPRIN sequences indicated above. The degree of identity between two amino acid sequences can be determined by conventional methods, for example, by means of standard sequence alignment algorithms known in the state of the art, such as BLAST (Altschul S. F. et al. Basic local alignment search tool. J Mol Biol. 1990; 215(3):403-10), for example. The person skilled in the art will understand that the amino acid sequences referred to herein can be chemically modified, for example, by means of chemical modifications that are physiologically relevant, such as, phosphorylations, acetylations, etc.

As it is used herein, the term "EMMPRIN inhibitor" or "inhibitors of a functionally equivalent EMMPRIN variant" refers to any compound binding specifically to EMMPRIN (or to the functionally equivalent variant thereof) and which, upon binding, is capable of causing a reduction of the activity of said protein or of reducing the EMMPRIN protein or mRNA levels. EMMPRIN inhibitors that act by inhibiting the function of said protein include, but are not limited to, (a) inhibition of MMP induction by EMMPRIN, for example inhibiting glycosylation or the interaction between MMPs and EMMPRIN (Toole 2003; Curr Top Dev Biol.; 54:371-89), inhibiting intracellular signaling through the p38 MAP kinase pathway or arachidonic acid metabolism (Taylor et al. Oncogene. 2002; 21(37):5765-72); (b) inhibition of MMP-14-mediated EMMPRIN processing (Egawa et al. J Biol. Chem. 2006; 281(49):37576-85); (c) inhibition of the EMMPRIN binding to cyclophilin (Gwinn et al. J Immunol. 2006; 177(7):4870-9); (d) inhibition of EMMPRIN expression (Curtin et al. Glia. 2007; 55(15):1542-53); (e) inhibition of EMMPRIN binding to monocarboxylate transporter (MCT-1) in astrocytes (Korn et al. Glia. 2005; 49(1):73-83).

The person skilled in the art will note that it is possible to use EMMPRIN inhibitors specific for proteins of different species, depending on the species in which the EMMPRIN inhibitor is to be used. Therefore, the invention contemplates human EMMPRIN protein inhibitors, as defined in the NCBI database with accession number NP940991 (SEQ ID NO:1) (version Jul. 18, 2010). However, the person skilled in the art will note that it is possible to use homologues of other mammal species, which include, but are not limited to, mouse (*Mus musculus*) EMMPRIN corresponding to the protein described in NCBI with accession number NP033898 (version from Jul. 18, 2010), rat (*Rattus norvegicus*) EMMPRIN corresponding to the protein described in the NCBI database with accession number NP036915 (version from Jul. 18, 2010), as well as chickens, pigs, bovine species, etc.

Figure 3:
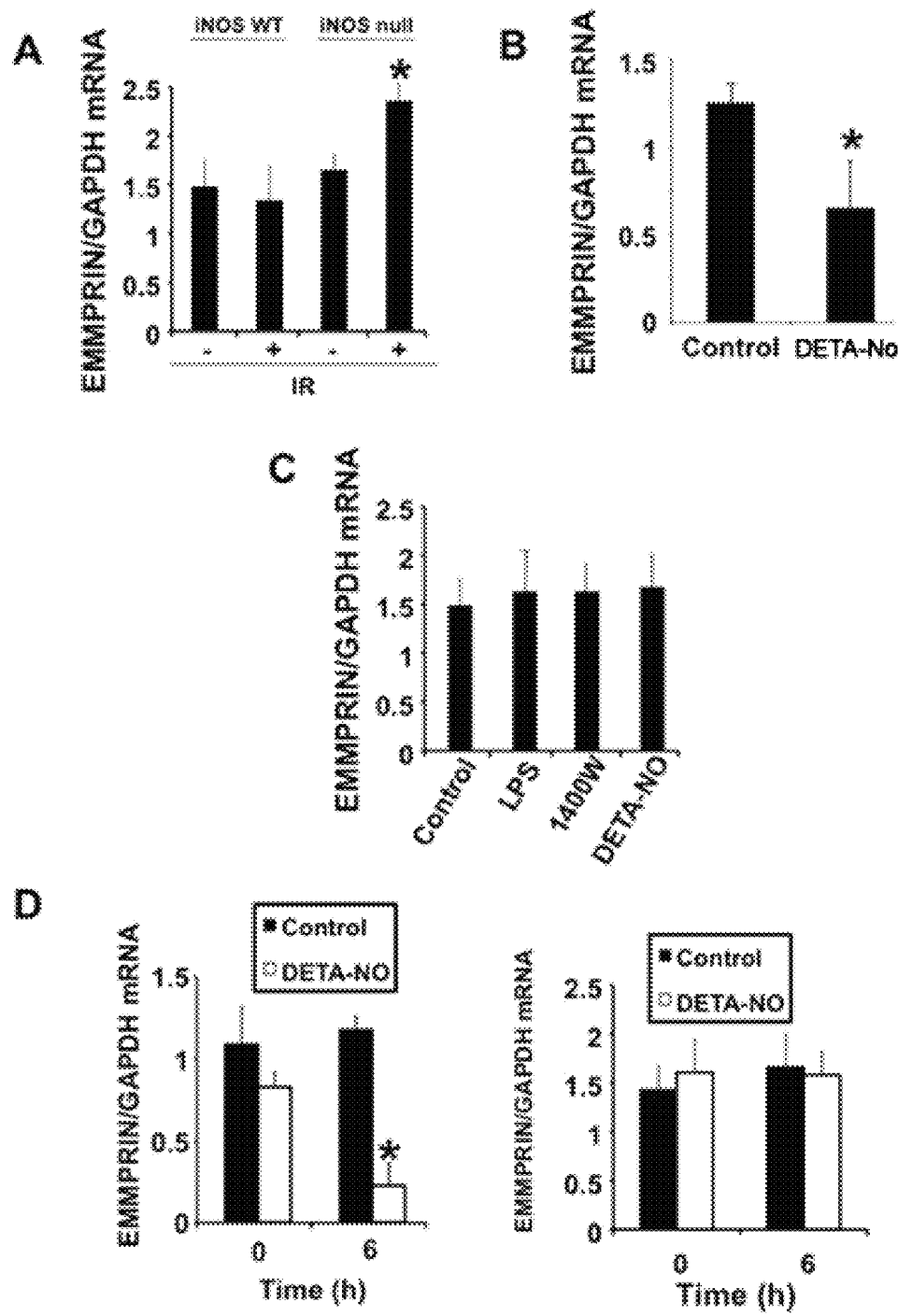
FIG. 3 shows that the absence of iNOS increases EMMPRIN mRNA levels in cardiomyocytes. (A) Quantitative real-time RT-PCR showing EMMPRIN expression in the hearts of wild-type and iNOS knockout animals after ischemia/reperfusion (n=3 in triplicate, mean±SD *p<0.05 vs iNOS null−). (B) Quantitative real-time RT-PCR showing EMMPRIN expression in HL1 cardiomyocytes in response to the exogenous administration of 100 µM DETA-NO (n=3, mean±SD *p<0.05). (C) Quantitative real-time RT-PCR showing EMMPRIN expression in RAW 247.6 macrophages in culture in response to the exogenous administration of 100 µM of DETA-NO, endogenous NO production (50 µM LPS), or iNOS inhibition by means of adding 100 µM 1400W (n=3 mean±SD). (D) Stability assay of EMMPRIN mRNA in HL-1 cardiomyocytes (left) and in RAW 247.6 macrophages (right) (n=3, mean±SD *p<0.05).

Methods suitable for determining those compounds that are EMMPRIN inhibitors comprise both methods based on the determination of EMMPRIN levels or the levels of mRNA encoding EMMPRIN in endothelial cells, such as those based on the capacity to reduce cardiac damage. Methods suitable for determining EMMPRIN inhibition include, for example, the method described in Example 4 of the present invention and shown in FIG. 3, in which EMMPRIN mRNA expression levels are measured.

Therefore in a particular embodiment of the invention, EMMPRIN expression levels are determined by measuring the expression levels of the mRNA encoding for the EMMPRIN protein. For this purpose, the biological sample can be treated in order to physically or mechanically break down the structure of the tissue or cell to release the intracellular components into an aqueous or organic solution to prepare the nucleic acids for further analysis. The nucleic acids are extracted from the sample by means of commercially available methods known by the person skilled in the art. The mRNA is extracted later from frozen or fresh samples by means of any of the standard methods in the art, for example Sambrook, J., et al., 2001 Molecular Cloning, a Laboratory Manual, $3^{rd}$ ed., Cold Spring Harbor Laboratory Press, N.Y., Vol. 1-3. All the advancements known for avoiding RNA degradation during the extraction process are preferably provided.

The amount of mRNA encoding EMMPRIN can be determined, for example, by means of hybridization or amplification assays including, but not limited to, Northern and Southern Blot and polymerase chain reaction (PCR) assays. A method for detecting EMMPRIN-specific mRNA includes the use of probes which are capable of hybridizing specifically with EMMPRIN mRNA or cDNA. The probe can be a complete cDNA chain or a fragment thereof, such as for example an oligonucleotide at least 7, 15, 30, 50, 100, 250 or 500 nucleotides long capable of hybridizing with the target mRNA or cDNA under strict conditions. mRNA detection is preferably carried out after the amplification of the cDNA obtained from the mRNA using known amplification techniques, such as polymerase chain reaction (PCR), real-time polymerase chain reaction (RT-PCR), ligase chain reaction (LCR), self-sustained sequence replication (3SR) also known as nucleic acid sequence based amplification (NASBA), Q-B-Replicase amplification, rolling circle amplification (RCA), transcription-mediated amplification (TMA), linker-aided DNA amplification (LADA), multiple displacement amplification (MDA), invader and strand displacement amplification (SDA).

On the other hand, the EMMPRIN protein level can be quantified by means of any conventional method that allows detecting and quantifying said protein in a sample from a subject. By way of non-limiting illustrative example, said protein levels can be quantified, for example, by means of using antibodies with the capacity to bind to EMMPRIN (or to fragments thereof that contain an antigenic determinant) and the subsequent quantification of the complexes formed. The antibodies used in these assays can be labeled or unlabeled. Illustrative examples of labels that can be used include radioactive isotopes, enzymes, fluorophores, chemiluminescent reagents, enzymatic substrates or cofactors, enzyme inhibitors, particles, dyes, etc. There is a wide range of known assays that can be used in the present invention, which use unlabeled antibodies (primary antibody) and labeled antibodies (secondary antibody); included among these techniques are Western blot, ELISA (enzyme-linked immunosorbent assay), RIA (radioimmunoassay), competitive EIA (competitive enzyme immunoassay), DAS-ELISA (double-antibody sandwich ELISA), immunocytochemical and immunohistochemical techniques, techniques based on the using protein biochips or microarrays which include colloidal precipitation-based assays or specific antibodies in formats such as dipsticks. Other ways of detecting and quantifying said EMMPRIN protein include affinity chromatography techniques, ligand binding assays, etc.

Western blot is based on detecting proteins previously separated by means of gel electrophoresis under denaturing conditions and immobilized on a membrane, generally a nitrocellulose or a PVDF (polyvinylidene difluoride) membrane, by means of incubating with a specific antibody and a developing system (for example, chemiluminescence). Immunofluorescent analysis requires using an antibody that is specific for the target protein to analyze expression. ELISA is based on using enzyme-labeled antibodies or antigens such that the conjugates formed between the target antigen and the labeled antibody result in the formation of enzymatically active complexes. Since one of the components (the labeled antibody or the antigen) are immobilized on a support, the antigen-antibody complexes are immobilized on the support and they can thus be detected by means of adding a substrate which the enzyme converts into a product that is detectable by means of spectrophotometry or fluorometry, for example.

When an immunological method is used, any antibody or reagent that is known to bind to EMMPRIN with a high enough affinity to detect the amount of target proteins can be used. However, the use of an antibody, for example polyclonal sera, hybridoma supernatants or monoclonal antibodies, antibody fragments, Fv, Fab, Fab' and F(ab')2, scFv, humanized antibodies, diabodies, triabodies, and tetrabodies, is preferred.

On the other hand, protein expression levels can be determined by means of immunohistochemical techniques well known in the state of the art. To perform the determination by means of immunohistochemistry, the sample can be a fresh sample, a frozen sample embedded in plastic material, or a fresh sample embedded in paraffin and fixed using a protective agent such as formalin. For the immunohistochemical determination, the sample is stained with an EMMPRIN-specific antibody and the amount of stained cells and the staining intensity are determined. A value indicative of the total expression which is calculated depending on the frequency of stained cells (a value ranging between 0 and 4) and on the intensity in each of the stained cells (value ranging between 0 and 4) is typically assigned to the sample. Standard criteria for assigning expression values to samples have been described in detail, for example, in the Handbook of Immunohistochemistry and In Situ Hybridization in Human Carcinomas, M. Hayat Ed., 2004, Academic Press. Immunohistochemical detection is preferably carried out in parallel with cell samples that serve as a positive marker and as a negative marker. A background control is also commonly used.

In those cases in which a large number of samples are to be analyzed, it is possible to use array formats and/or automated methods. In one embodiment, it is possible to use tissue microarrays (TMAs) that can be obtained using different techniques. The samples that are part of the microarrays can be analyzed in a different way, including immunohistochemistry, hybridization in situ, PCR in situ, RNA or DNA analysis, morphological inspection and combinations of any of the foregoing. Methods for processing tissue microarrays have been described, for example, in Konenen, J. et al., (Nat. Med. 1987, 4:844-7). The tissue microarrays are prepared from cylindrical cores ranging from 0.6 to 2 mm in diameter from tissue samples embedded in paraffin and again embedded in a single receptor block. Tissue from multiple samples can therefore be inserted in a single block of paraffin.

According to the present invention, "reduced EMMPRIN mRNA or protein levels" in relation to mRNA or protein levels in a reference sample, are understood as a decrease in mRNA or protein levels of at least 1.1 fold, 1.5 fold, 5 fold, 10 fold, 20 fold, 30 fold, 40 fold, 50 fold, 60 fold, 70 fold, 80 fold, fold, 100 fold or even more with respect to the control sample from the subject. According to the present invention, "reference or control levels" are understood as EMMPRIN mRNA or protein levels that the subject has before being administered the EMMPRIN inhibitors or to which subject control inhibitors that do not inhibit EMMPRIN have been administered.

As it is used herein, the term "ischemia" refers to ischemic heart disease or myocardial ischemia, characterized by reduced supply of blood to the heart muscle, the necessary oxygen and nutrient levels thereby decreasing. A fairly common cause of myocardial ischemia is atherosclerosis of the coronary arteries, which causes a blockage in the coronary arteries supplying blood to the heart muscle. After ischemia, oxygen and nutrient deprivation means that the cells, tissues and organs begin a degradation process that ends in cell death. The absence of oxygen and nutrients in the blood creates a condition in which blood circulation restoration results in inflammation and damage due to the induction of oxidative stress. The term "ischemia followed by reperfusion" is used interchangeably with "ischemia/reperfusion" throughout the present specification.

The term "cardiac damage after ischemia followed by reperfusion" refers to heart tissue damage if the blood flow is restored in the region of the tissue that was deprived of blood supply. The EMMPRIN inhibitor allows reducing or minimizing the extent and/or severity of said damage caused in the heart during the ischemia/reperfusion event, specifically with regard to infarct size and cardiac remodeling. Examples of "cardiac damage after ischemia followed by reperfusion" include, but are not limited to, ischemic necrosis or infarct, adverse cardiac remodeling, permanent heart tissue damage, permanent coronary occlusion, acute cell death, ventricular function deterioration, etc.

Likewise, the EMMPRIN inhibitor can be used prophylactically to prevent myocardial damage in a subject who is at risk of developing damage due to myocardial ischemia, for example, due to a myocardial infarct, including reducing cell death and/or the presence of myocardial edema and/or myocardial infarcts. Other conditions that can place a subject at risk of suffering ischemia-associated cardiac damage includes genetic predisposition to myocardial infarct or a condition which is understood to increase the probability of myocardial ischemia, such as atherosclerosis, prior myocardial infarct or prior transient ischemic attacks, diabetes mellitus, hypertension, hypercholesterolemia or being a smoker.

As a person skilled in the art will note, damage caused in heart tissue after ischemia/reperfusion can be determined using imaging techniques such as echocardiography, magnetic resonance imaging (MRI), computerized tomography (CT) of the heart and nuclear scans of the heart. Additionally, cardiac damage leads to the increase of one or more markers, including troponin, CK-MB (creatine kinase MB) and CPK (creatine phosphokinase), which are indicative of myocardial death and can also be measured to ascertain cardiac damage.

In the context of the present invention, when using the expression "reduction or treatment of cardiac damage", it refers to a reduction of said damage by 5%, 10%, 20%, 30%, 40%, or even a 50% reduction of cardiac damage caused by ischemia/reperfusion. The drop or reduction can alternatively be 60%, 70% or 80%.

The EMMPRIN inhibitor is administered to a subject either alone or in combination with other compounds and comprises a therapeutically effective amount of said inhibitor. As it is used herein, the expression "therapeutically effective amount" refers to the amount of EMMPRIN inhibitor calculated to cause the desired effect, and it will generally be determined, among others, by the characteristics typical of said inhibitor and the therapeutic effect to be achieved. Therefore, the administered amount and the duration of treatment are effective for minimizing the size and/or severity of cardiac damage in the subject measured, for example, as an increase of the ejection fraction in the heart, less cell death in the myocardium or reduction of ischemia-associated myocardial edema. The amount and the duration of treatment are determined by a person skilled in the art. The EMMPRIN inhibitor can be administered during the ischemic process. It can alternatively be administered after the ischemia occurred, but before reperfusion occurs, or alternatively after ischemia and during reperfusion, or after ischemia and after reperfusion.

The EMMPRIN inhibitors can be administered by any suitable route, including, but not limited to, orally, by inhalation, rectally, by subcutaneous route, intradermal route, intravenous route, intramuscular route, intraarterial route, intramedullary route, intrathecal route, intraventricular route, by means of percutaneous transluminal coronary angioplasty (with a balloon or PTCA), through a stent, transdermal route, subcutaneous route, intraperitoneal route or intranasal route. A review of the different dosage forms can be found in the Tratado de Farmacia Galénica, C. Faulí i Trillo, Luzán 5, S. A. de Ediciones, 1993.

In a particular embodiment, the invention relates to the use of an EMMPRIN inhibitor, wherein said inhibitor is selected from the group consisting of an anti-EMMPRIN antibody, an siRNA, a glycosylation modulator, an inhibitory peptide, a cyclophilin-EMMPRIN binding inhibitor, a statin, a p53 activator, a PPAR-alpha antagonist, an antisense oligonucleotide, a ribozyme, an aptamer and a Spiegelmer.

Other agents inhibiting EMMPRIN expression suitable for use in the present invention are, for example, cynaropicrin (CAS number 35730-78-0), which modulates nitric oxide production, as described by Cho et al. (Biophysical Research Communications, 2004; 313:954-961), polynucleotides with decoy activity, i.e., with the capacity to bind specifically to a transcription factor that is important for expression of the gene, such that the expression of the gene of interest, in this case EMMPRIN, is inhibited, and organic molecules binding to EMMPRIN inhibiting its activity, etc.

In a particular embodiment, the invention contemplates the use of an EMMPRIN inhibitor in combination with a therapy aimed at treating damage caused by ischemia/reperfusion, which will be determined by a person skilled in the art. Treatments that can be combined with the use of the EMMPRIN inhibitor are, but are not limited to, the administration of hydrogen sulfide (Elrod J. W et al. Circulation 2006; 114: 1172), thrombolytic therapy, percutaneous coronary intervention, by-pass surgery, administration of anti-platelet agents, anticoagulant agents, etc. (Cannon R O. Nat Clin Pract Cardiovasc Med 2005; 2:88).

Anti-EMMPRIN Antibodies

In the context of the present invention, "anti-EMMPRIN antibody" is understood as any antibody that is capable of binding specifically to EMMPRIN causing the inhibition of one or more functions of EMMPRIN. It is also any antibody that is capable of binding specifically to EMMPRIN and blocking the oligomerization of EMMPRIN or EMMPRIN binding sites with other proteins. Anti-EMMPRIN antibodies specifically target protein epitopes essentially for carrying out their function or the whole protein. The antibodies can be prepared using any of the methods known to the person skilled in the art. Therefore, polyclonal antibodies are prepared by means of immunizing an animal with the protein to be inhibited. Monoclonal antibodies are prepared using the method described by Kohler, Milstein et al. (Nature, 1975, 256: 495). In the context of the present invention, suitable antibodies include intact antibodies comprising an antigen binding variable region and a constant region, "Fab", "F(ab")2" and "Fab", Fv and scFv fragments, bispecific antibodies and diabodies.

Any antibody targeting the EMMPRIN protein can be used as an inhibitor. In a particular embodiment, the antibody specifically recognizes the N-terminal end of EMMPRIN, which corresponds to the extracellular domain. In an even more preferred embodiment, the anti-EMMPRIN antibody has been generated against the N-terminal end of EMMPRIN. In an even more preferred embodiment, the anti-EMMPRIN antibody has been generated using the third Ig-like domain, as described by Hanna, S. M. et al. (BMC Biochemistry, 2003 4:17) formed, in the case of human CD147, by the sequence

```
  1 AGFVQAPLSQ QRWVGGSVEL HCEAVGSPVP EIQWWFEGQG
    PNDTCSQLWD GARLDRVHIH

61 ATYHQHAAST ISIDTLVEED TGTYECRASN DPDRNHLTRA
    PRVKWVRAQA VVLVLEPGT (SEQ ID NO: 2)
``` or an antibody generated against the first and/or against the second Ig-like domain.

Other antibodies with the capacity to inhibit EMMPRIN activity include, but are not limited to, HBJ127 antibody described by Itoh et al. (Jpn. J. Cancer Res., 2001, 92:1313-1321); the antibody described in WO2010036460A2; the murine monoclonal antibodies described in Ellis et al. (Cancer Res 1989; 49:3385-91) and MEM-M6/6 antibody described in Koch, et al. 1999; Internat. Immunol. 11: 777-786; a murine IgM monoclonal antibody, CBL1 (Billings et al. Hybridoma 1:303-311, 1982, U.S. Pat. Nos. 5,330,896 and 5,643,740); antibody targeting the transmembrane domain of the extracellular domain (US2007048305A1). Anti-EMMPRIN specific antibodies also include commercial antibodies, such as those from Santa Cruz Biotechnology (G19 and T18), which are polyclonal antibodies targeting mouse EMMPRIN and generated in goat; the antibody from E-bioscience, clone RL73.2 (Renno et al. J Immunol. 2002; 168(10):4946-50); the monoclonal antibody derived from the UM-8D6 clone targeting human EMMPRIN and is commercially available from Ancell; the gavilimonab (ABX-CBL) monoclonal antibody from Abgenix and the ziralimunab antibody from Abgenix, both targeting human EMMPRIN, etc.

Glycosylation Modulators

EMMPRIN is a highly glycosylated protein, different variants of the protein being able to be generated according to the glycosylation level. EMMPRIN-mediated MMP induction is glycosylation-dependent (Sun et al. Cancer Res. 2001; 61:2276-2281), and therefore the inhibition of glycosylation prevents EMMPRIN from inducing MMP activity and suitably carrying out the function thereof (Tang et al. Mol Biol Cell. 2004; 9:4043-4050). Examples of glycosylation inhibitors include, but are not limited to, tunicamycin (inhibitor of the N-linked glycosylation), UCHL-1, etc. Glycosylation can also be modulated through different types of endoglycosidases, which cleave EMMPRIN oligosaccharides, once it is glycosylated. Examples of endoglycosidases include, but are not limited to, endoglycosidase D, endoglycosidase F, endoglycosidase F1, endoglycosidase F2 and endoglycosidase H. Glycosylation modulation in EMMPRIN can be ascertained by means of Western blot because once glycosylation is eliminated, the glycosylated forms of EMMPRIN disappear, a single protein band corresponding to the non-glycosylated form appearing.

Inhibitory Peptides of EMMPRIN

In a particular embodiment, the invention contemplates the use of inhibitory peptides of EMMPRIN for preventing and/or reducing cardiac damage after ischemia followed by reperfusion.

The peptide or functional analogue or derivative of said inhibitory peptide is capable of binding to the EMMPRIN protein, inhibiting its function. AP-9 antagonist peptide or a functional analogue or derivative thereof is one of the peptides that can be used as an EMMPRIN inhibitor, its function being described in the literature (Zhou et al. BMC Cell Biology 2005, 6:25). The sequence of AP-9 peptide corresponds to the amino acid sequence YKLPGHHHHYRP (SEQ ID NO: 3). It is thought that AP-9 peptide can inhibit dimerization of EMMPRIN and between EMMPRIN and the MMPs (Yang et al. Rheumatology 2008, 47: 1299-1310).

A functional analogue or derivative of said inhibitory peptide has an amino acid sequence that has been altered, such that the functional properties of the sequence are essentially the same, although it can have a different inhibition level. Assays that are valid for knowing if an analogue or derivative of the inhibitory peptide is capable of inhibiting the EMMPRIN protein are those in which a reduction of said protein, or of any of its targets such as MMPs in this case, is observed by means of techniques that allow carrying out a quantification process, such as Western blot, but those techniques based on determining the tested inhibitor's capacity to reduce cardiac damage will also be valid. The analogue or derivative can have conservative amino acid substitutions, such that one amino acid is substituted with another with similar characteristics (size, hydrophobicity, etc.) without the general function being seriously affected, i.e., it conserves the EMMPRIN inhibition capacity. Peptide mimetic compounds can also be designed such that they are functionally or structurally similar, using the original peptide as the starting point. However, it is usually desirable to improve a specific function. A derivative can come from a systematic improvement of at least one property of said amino acid sequence. Multiple peptides can be generated based on the original amino acid sequence by means of the Ala-scanning technique, for example, each containing the substitution of at least one amino acid. Peptides with an improved function can thus be designed. Derivatives or analogues of inhibitory peptides can be generated by substituting an amino acid residue in the form of L-amino acid with the same amino acid in the form of D-amino acid, being able to improve the properties of the peptide. A person skilled in the art will be capable of generating analogue compounds of the amino acid sequence of the inhibitory peptide, for example, based on a search in a peptide library. The inhibitory peptide can also be found in circular form, it can be in tandem or repeated configuration form, conjugated or bound to carriers known in the state of the art.

EMMPRIN-cyclophilin Binding Inhibitors

In a particular embodiment, the invention contemplates the use of an EMMPRIN-cyclophilin binding inhibitor. Cyclophilins are members of the immunophilin family of isomerases. They have been described as EMMPRIN cell surface expression regulators; it has specifically been described that cyclophilin binds to EMMPRIN through the transmembrane region, the proline residue in position 211 being essential for said interaction (Yurchenko et al. 2005. J Biol Chem 280:17013-19) and it could act as a chaperone (Pushkarsky et al. The Journal of Biological Chemistry, 280: 27866-27871). Therefore, a molecule that binds to cyclophilin, preventing cyclophilin from interacting with EMMPRIN, would prevent the correct folding of EMMPRIN, with the subsequent loss of EMMPRIN activity. Examples of cyclophilin-EMMPRIN binding inhibitors include, but are not limited to, cyclosporine A, its analogue Debio 025 or alisporivir (CAS registry no. 254435-95-5), non-immunosuppressive cyclosporine A analogues SCY635 and NIM811, antibodies targeting cyclophilin, organic molecule inhibitors of cyclophilin, etc.

Statins

Another aspect of the invention contemplates the use of statins as EMMPRIN inhibitors. Statins are capable of inhibiting EMMPRIN expression (Abe N et al. Life Sci 2006; 78:1021-8). Examples of statins that can be used for EMMPRIN inhibition in the present invention include, but are not limited to, fluvastatin (CAS registry no. 93957-54-1), atorvastatin (CAS registry no. 134523-03-8), cerivastatin (CAS registry no. 145599-86-6), lovastatin (CAS registry no. 75330-75-5), mevastatin (CAS registry no. 73573-88-3), pitavastatin (CAS registry no. 147511-69-1), pravastatin (CAS registry no. 81093-37-0), rosuvastatin (CAS registry no. 287714-41-4), simvastatin (CAS registry no. 79902-63-9), and derivatives thereof.

p53 Activators

In a particular embodiment, the invention contemplates the use of a p53 activator as an EMMPRIN inhibitor. p53 activity has been inversely related to the amount of EMMPRIN expressed in cells (Zhu H et al. Cancer Biol Ther. 2009; 8(18):1722-8). Therefore, an increase of p53 activity would entail a decrease of EMMPRIN, which allows using compounds increasing p53 activity as EMMPRIN inhibitors in the present invention. Examples of p53 activators include, but are not limited to, nutlin (Roche, CAS registry no. 548472-68-0), proteins that phosphorylate p53, such as DNA-dependent protein kinase (DNA-PK) or ATM kinase, ARF protein, any compound that increases p53 activity, either directly or indirectly, as well as expression vectors known to the person skilled in the art that express p53, etc.

PPAR-alpha Agonists

In another aspect of the invention, the use of PPAR-alpha agonists as EMMPRIN inhibitors is contemplated. PPAR-alpha agonists are known to inhibit EMMPRIN expression in macrophages and in foam cells (Zhang J et al. Int J Cardiol. 2007 117:373-80). Therefore, PPAR-alpha activators or agonists are useful for the present invention. Said activators can act directly or indirectly on PPAR-alpha, such that PPAR-alpha activity increases considerably. Examples of PPAR-alpha agonists include, but are not limited to, gemfibrozil, fenofibrate, bezafibrate, clofibrate, ciprofibrate, fenofibrate, etc.

PPAR-alpha Antagonists

In another aspect of the invention, the use of PPAR-alpha antagonists as EMMPRIN inhibitors is contemplated. Activation of the peroxisome proliferator-activated receptor alpha (PPAR-alpha) is known to increase EMMPRIN mRNA levels (Konig B et al. Mol Nutr Food Res. 2010; 54:1248-56). Therefore, PPAR-alpha inhibitors or antagonists are useful for the present invention. Said inhibitors can act directly or indirectly on PPAR-alpha, such that PPAR-alpha activity drops considerably. Examples of said antagonists include, but are not limited to, PPAR-alpha phosphorylation inhibitors, 2-chloro-5-nitro-N-(pyridyl)benzamide, etc.

Other EMMPRIN Inhibitors

One of the inhibitors described for EMMPRIN is caveolin-1, which is associated with EMMPRIN in multiple cell types, including endothelial cells and smooth muscle cells. Caveolin-1 is known to be a negative regulator of the association of EMMPRIN with other EMMPRIN molecules and therefore inhibits MMP induction activity (Tang et al. Mol Biol Cell. 2004; 9: 4043-4050).

On the other hand, inhibiting the homophilic interaction of EMMPRIN is possible by means of using soluble EMMPRIN which competes for the binding site of the other EMMPRIN molecule (Sun et al. Cancer Res. 2001; 61:2276-2281).

siRNA of the Invention

Small interfering RNAs or siRNAs are agents that are capable of inhibiting the expression of a target gene by means of RNA interference. siRNA can be chemically synthesized, can be obtained by means of in vitro transcription or can be synthesized in vivo in the target cell. siRNAs typically consist of double stranded RNA between 15 and 40 nucleotides long that can contain a 3' and/or 5' overhang region 1 to 6 nucleotides long. The length of the overhang region is independent of the total length of the siRNA molecule. siRNAs act by means of post-transcriptional silencing or degradation of the target messenger.

siRNAs can be the so-called shRNAs (short hairpin RNAs) characterized in that the anti-parallel strands forming the siRNA are connected by a loop or hairpin region. These siRNAs are made up a short antisense sequence (from 19 to 25 nucleotides long), followed by a loop between 5 and 9 nucleotides longs followed by the sense strand. shRNAs can be encoded by plasmids or viruses and be under the control of promoters such as the U6 RNA polymerase III promoter.

The siRNAs of the invention are substantially homologous to EMMPRIN mRNA or to the genomic sequence encoding said protein. "Substantially homologous" is understood as having a sequence that is sufficiently complementary or similar to the target mRNA such that the siRNA is capable of causing the degradation of the former by RNA interference. The siRNAs suitable for causing said interference include siRNAs formed by RNA, as well as siRNAs containing different chemical modifications such as:

siRNAs in which the bonds between nucleotides are different from those that are found in nature, such as phosphorothioate bonds.

Conjugates of the RNA strand with a functional reagent, such as a fluorophore.

Modifications of the ends of the RNA strands, particularly the 3' end, by means of modification with different functional groups of the hydroxyl in position 2'.

```
(1): Sense: r(GGG AAU GCU CCA AAC GAC A)dTdT    Antisense: r(UGU
            (SEQ ID NO: 16).                               CGU UUG GAG CAU UCC C)dTdT (SEQ ID NO: 17).

(2) Sense:  r(GGA UCA AGG UCG GAA AGA A)dTdT    Antisense: r(UUU
            (SEQ ID NO: 18).                               UUU CCG ACC UUG AUC C)dTdT (SEQ ID NO: 19).

(3) Sense   r(GAG CCU UAC CUU ACA GAA A)dTdT    Antisense: r(UUU CUG
            (SEQ ID NO: 20).                               UAA GGU AAG GCU C)dTdT (SEQ ID NO: 21)

(4) Sense   r(GCA GUG ACC CAG ACC GCA A)dTdT    Antisense: r(UUG CGG
            (SEQ ID NO: 22).                               UCU GGG UCA CUG C)dTdT (SEQ ID NO: 23)
```

Nucleotides with modified sugars such as O-alkylated moieties in position 2' such as 2'-O-methylribose-p-2'-O-fluororibose.

Nucleotides with modified bases such as halogenated bases (for example 5-bromouracil and 5-iodouracil), alkylated bases (for example 7-methylguanosine).

The siRNAs and shRNAs of the invention can be obtained using a series of techniques known to the person skilled in the art. For example, the siRNA can be chemically synthesized from ribonucleosides protected with phosphoramidites in a conventional DNA/RNA synthesizer. The siRNAs can alternatively be produced in a recombinant manner from plasmid and viral vectors in which case the region encoding the strand or strands forming the siRNAs are under the operative control of RNA polymerase III promoters. Dicer RNAse processes the shRNAs into functional siRNAs in cells.

The EMMPRIN region that is used as a basis for designing siRNAs is not limiting and can contain a region of the coding sequence (between the start codon and the stop codon), or it can alternatively contain sequences of the non-translated 5' or 3' region, is preferably between 25 and 50 nucleotides long and in any position in 3' position with respect to the start codon. One way of designing an siRNA involves identifying the AA(N19)TT motifs, wherein N can be any nucleotide in the EMMPRIN sequence and by selecting those having a high G/C content. If said motif is not found, it is possible to identify NA(N21) motif, wherein N can be any nucleotide.

The EMMPRIN-specific siRNAs that can be used include any siRNA specifically targeting the EMMPRIN protein of the species which is to be inhibited. Examples of siRNA include, but are not limited to, siRNAs synthesized by means of the Silencer siRNA construction kit by Ambion Research Inc., such as siRNA of sequence 5' AAGACCTTGGCTCCAAGATACCCTGTCTC 3'(SEQ ID NO: 4)-AAGTATCTTGGAGCCAAGGTCCCTGTCTC (SEQ ID NO: 5) (Kulandaivelu et al. J Biol Chem. 2008; 283(28): 19489-19498), siRNA of sequence 5'-GUUCUUCGUGAGUUCCUCdTdT-3' (SEQ ID NO: 6)-3' dTdT-CAAGAAGCACUCAAGGAG 5' (SEQ ID NO: 7) (Chen et al. Cancer Letters 278 (2009) 113-121), siRNA of sequence 5' GGUUCUUCGUGAGUUCCUCtt 3' (SEQ ID NO: 8)-3' GAGGAACUCACGAAGAACCtg 5' (SEQ ID NO: 9) (Qian et al. Journal of Experimental & Clinical Cancer Research 2008, 27:50), siRNAs of sequence 5' GUAGGACCGGCGAGGAAUA 3' (SEQ ID NO: 10), 5' GACCUUGGCUCCAAGAUAC 3' (SEQ ID NO: 11), 5' GUCGUCAGAACACAUCAAC 3'(SEQ ID NO: 12), 5' GAUCACUGACUCUGAGGAC 3' (SEQ ID NO: 13), 5' UGACAAAGGCAAGAACGUC 3' (SEQ ID NO: 14), 5' GUUGGGUUUUCUCCAUUCA 3' (SEQ ID NO: 15), described in patent application WO06039343A, etc. The invention contemplates the use of other siRNAs such as the following, synthesized by Qiagen:

Antisense Oligonucleotides

An additional aspect of the invention refers to the use of "antisense" nucleic acids for inhibiting expression, for example by inhibiting the transcription and/or translation of a nucleic acid encoding EMMPRIN and the activity of which is to be inhibited. Antisense nucleic acids can be bound to the potential target of the drug by means of conventional base complementarity, or, for example, in the case of binding to double-stranded DNA, through specific interactions in the major groove of the double helix. These methods generally refer to the range of techniques generally used in the art and include any method that is based on the specific binding to oligonucleotide sequences.

An antisense construct of the present invention can be distributed, for example, like an expression plasmid which, when transcribed in the cell, produces RNA that is complementary to at least one unique part of the cellular mRNA encoding EMMPRIN. Alternatively, the antisense construct is an oligonucleotide probe which is generated ex vivo and which, when introduced in the cell, causes gene expression inhibition by hybridizing with the mRNA and/or genomic sequences of a target nucleic acid. Such oligonucleotide probes are preferably modified oligonucleotides which are resistant to endogenous nucleases, for example, exonucleases and/or endonucleases, and which are therefore stable in vivo. Exemplary nucleic acid molecules for use as antisense oligonucleotides are phosphoramidate, phosphothionate and methylphosphonate analogues of DNA (also see U.S. Pat. Nos. 5,176,996; 5,264,564; and 5256775). Additionally, general approaches for constructing oligomers useful in antisense therapy have been reviewed, for example, in Van der Krol et al., BioTechniques 6: 958-976, 1988; and Stein et al., Cancer Res 48: 2659-2668, 1988.

With respect to the antisense oligonucleotide, the oligodeoxyribonucleotide regions derived from the translation start site, for example, between −10 and +10 of the target gene, are preferred. Antisense approaches involve designing oligonucleotides (either DNA or RNA) that are complementary to the mRNA encoding the target polypeptide. The antisense oligonucleotides will bind to the mRNA transcripts and prevent translation.

The antisense oligonucleotides can be from single- or double-stranded DNA or RNA, chimeric mixtures or derivatives or modified versions thereof. The oligonucleotide can be modified in the base group, the sugar group or the phosphate backbone, for example, to improve stability of the molecule, its hybridization capacity, etc. The oligonucleotide can include other bound groups, such as peptides (for example, to direct them to host cell receptors) or agents for facilitating transport through the cell membrane (see, for example, Letsinger et al., Proc. Natl. Acad. Sci. U.S.A. 86:6553-6556, 1989; Lemaitre et al., Proc. Natl. Acad. Sci. 84:648-652, 1987; PPCT Publication No. WO88/09810), intercalating agents (see, for example, Zon, Pharm. Res. 5: 539-549, 1988). For this purpose, the oligonucleotide can be conjugated to another molecule, for example, a peptide, a carrier agent, hybridization-triggered cleaving agent, etc.

To carry out the invention, antisense oligonucleotides complementary to the coding region of the target sequence of EMMPRIN mRNA, as well as those complementary to the non-translated transcribed region can be used. A non-limiting example of antisense oligonucleotides that can be used is the antisense oligonucleotide described in US2005026841A, the sequence of which is 5' GAGCTA-CACATTGAGAACCTG 3'(SEQ ID NO: 24).

DNA Enzymes

Another aspect of the invention refers to the use of DNA enzymes for inhibiting the expression of the gene encoding the EMMPRIN protein. DNA enzymes incorporate some of the mechanistic characteristics both of antisense technology and of ribozyme technology. DNA enzymes are designed such that they recognize a particular nucleic acid target sequence, similar to the antisense oligonucleotide and similar to the ribozyme in which they are catalytic and specifically digest the target nucleic acid. Examples of DNA enzymes specifically aimed at inhibiting EMMPRIN include, but are not limited to, the following DNA sequences described in WO2006039343:

```
TGATTCCTAGGCTAGCTACAACGATCCTCGCCG
(SEQ ID NO: 25),

CAGCGCGAAGGCTAGCTACAACGACCCAGCAGC
(SEQ ID NO: 26),

TGAGGAGTAGGCTAGCTACAACGACTTGGAGCC
(SEQ ID NO: 27),

TGATCACCAGGCTAGCTACAACGAGCCCCCCTT
(SEQ ID NO: 28),

GGAGCTGGAGGCTAGCTACAACGAGTTGGCCGT
(SEQ ID NO: 29),

CCTCGTTGAGGCTAGCTACAACGAGTGTTCTGA
(SEQ ID NO: 30),

AGTCAGTGAGGCTAGCTACAACGACTTGTACCA
(SEQ ID NO: 31),

CGGCCTCCAGGCTAGCTACAACGAGTTCAGGTT
(SEQ ID NO: 32),

GGAGCGTGAGGCTAGCTACAACGAGATGGCCTG
(SEQ ID NO: 33),

GCACCAGCAGGCTAGCTACAACGACTCAGCCAC
(SEQ ID NO: 34),

CCTTTGTCAGGCTAGCTACAACGATCTGGTGCT
(SEQ ID NO: 35).
```

Ribozymes

Another aspect of the invention contemplates the use of ribozyme molecules designed for catalytically cleaving transcripts of a target mRNA to prevent translation of the mRNAs encoding EMMPRIN and the activity of which is to be inhibited. Ribozymes are enzymatic RNA molecules capable of catalyzing specific RNA cleaving (see, Rossi, Current Biology 4:469-471, 1994). The mechanism of action of the ribozyme involves sequence-specific hybridization of the ribozyme molecule with a complementary RNA target, followed by an endonucleolytic cleavage event. The composition of the ribozyme molecules preferably includes one or more sequences complementary to the target mRNA and to the well known sequence responsible for cleaving mRNA or a functionally equivalent sequence (see, for example, U.S. Pat. No. 5,093,246).

The ribozymes used in the compositions of the present invention include hammerhead ribozymes, endoribonuclease RNA (Cech type) (Zaug et al., Science 224:574-578, 1984). The ribozymes can be made up of modified oligonucleotides (for example to improve stability, directing, etc.) and should be distributed to cells that express the target gene in vivo. A preferred distribution method involves using a DNA construct "encoding" the ribozyme under the control of a strong constitutive pol III or pol II promoter, such that the transfected cells will produce sufficient amounts of the ribozyme to destroy the endogenous target messengers and inhibit translation. Since ribozymes are catalytic, unlike other antisense molecules, lower intracellular concentration is required for their efficacy.

Aptamers and Spiegelmers

Other compounds with EMMPRIN expression inhibition capacity are aptamers and Spiegelmers, which are single- or double-stranded D or L nucleic acids binding specifically to the protein, which results in a modification of the biological activity of said protein. Aptamers and Spiegelmers are between 15 and 80 nucleotides long, and preferably between 20 and 50 nucleotides long.

Nanoparticles of the Invention

In another aspect, the invention relates to a nanoparticle, hereinafter nanoparticle of the invention, comprising on its surface a molecule with EMMPRIN binding capacity.

As it is used herein, the term "nanoparticle" refers to any particle having at least one of its dimensions smaller than about 1000 nm. The person skilled in the art is capable of obtaining nanoparticles as needed. The diameter of the nanoparticles can be about 5 nm or 10 nm or 20 nm or 30 nm or 40 nm or 50 nm or 60 nm or 70 nm or 80 nm or 90 nm or 100 nm or 200 nm or even larger.

The nanoparticles according to the invention comprise a biocompatible outer shell and on its surface a molecule with EMMPRIN binding capacity. Illustrative examples of components of the biocompatible outer shell include, but are not limited to any biodegradable polymer, such as those described in U.S. Ser. No. 12/519,590 (for example aliphatic polyesters, poly(glycolic acid), polyvinylpyrrolidone, polyethylene glycol (PEG), poly(lactic acid), polyalkylene succinate, polyhydroxybutyrate, polyhydroxyvalerate, polycaprolactone, poly(n-butyl methacrylate), poly(lactic-co-glycolic acid) and co-polymers derived therefrom, phospholipids, dextrans, silica and natural virus or lipoprotein shells. In a preferred embodiment, the outer shell comprises a layer of phospholipids.

Phospholipids suitable for use in the nanoparticles of the invention include, but are not limited to, phosphatidylserine (PS), dipalmitoyl and distearoyl phosphatidic acid (DPPA, DSPA), dipalmitoyl and distearoyl phosphatidylserine (DPPS, DSPS), dipalmitoyl, distearoyl phosphatidylglycerol (DPPG, DSPG), phosphatidylglycerol, phosphatidylinositol, cardiolipin, sphingolipids (cermide-1-phosphate, glycosylated phosphatidylethanolamine; sulfatides (hydroxylated or non-hydroxylated); gangliosides), phosphatidylinositol phosphates and phosphatidic acid. In an even more preferred embodiment, the layer of phospholipids is formed by phosphatidylcholine wherein the fatty acids can be any long-chain aliphatic acid (alkanoic acids) having variable chain length, from about $C_{12}$ to $C_{22}$, which contains one or more unsaturations or no unsaturations. The fatty acid is preferably selected from the group consisting of stearic acid (18:0 or octadecanoic acid), oleic acid (18:1 cis-9 or (9Z)-octadec-9-enoic acid), palmitic acid (16:0 or hexadecanoic acid), linoeic acid (18:2 (ω-6) or cis, cis-9,12-octadecadienoic acid), arachidonic acid (20:4 (ω-6) or all cis-5,8,11,14-eicosatetranoic acid), docosohexanoic acid (22:6 (n-3 or 4Z,7Z,10Z,13Z,16Z,19Z)-docosa-4,7,10,13,16,19-hexanoic acid). In a preferred embodiment, the nanoparticles comprise distearoylphosphatidylcholine (DSPC).

In an even more preferred embodiment, part or all of the phospholipid molecules forming the nanoparticle are modified by means of the binding of a molecule with EMMPRIN binding capacity.

As it is used herein, the expression "molecule with EMMPRIN binding capacity" refers to a molecule having affinity for EMMPRIN, such that the nanoparticles specifically target EMMPRIN. In a particular embodiment, the molecule with EMMPRIN binding capacity is selected from the group consisting of an inhibitory peptide of EMMPRIN and an anti-EMMPRIN antibody. If the molecule with EMMPRIN binding capacity is an anti-EMMPRIN antibody, said antibody targets extracellular domain of EMMPRIN. In a particular embodiment, the anti-EMMPRIN antibody is generated against the N-terminal end of EMMPRIN. In a preferred embodiment, the molecule with EMMPRIN binding capacity is the inhibitory peptide of EMMPRIN AP-9, the sequence of which corresponds to SEQ ID NO: 3.

The bond between the phospholipid molecules and the molecule with EMMPRIN binding capacity is formed by means of incorporating in the nanoparticles phospholipids modified by means of functional groups that can be conjugated with reagent residues present in the molecule with EMMPRIN binding capacity. As understood herein, functional groups refer to a group of specific atoms in a molecule that are responsible for a chemical reaction characteristic of said molecule. Examples of functional groups include, but are not limited to, hydroxy, aldehyde, alkyl, alkenyl, alkinyl, amide, carboxamide, primary, secondary, tertiary and quaternary amines, aminooxy, azide, azo (diimide), benzyl, carbonate, ester, ether, glyoxylyl, haloalkyl, haloformyl, imine, imide, ketone, maleimide, isocyanide, isocyanate, carbonyl, nitrate, nitrite, nitro, nitroso, peroxide, phenyl, phenyl, phosphine, phosphate, phosphone, pyridyl, sulfide, sulfonyl, sulfinyl, thioester, thiol and oxidized 3,4-dihydroxy phenylalanine (DOPA) groups.

In the specific case in which the molecule with EMMPRIN binding capacity is a protein or peptide, it is preferable to use groups of the maleimide or glyoxylyl type which react specifically with thiol groups in the molecule with EMMPRIN binding capacity and oxidized 3,4-dihydroxy phenylalanine (DOPA) groups reacting with primary amino groups in the molecule with EMMPRIN binding capacity.

In a preferred embodiment, the phospholipid and the molecule with EMMPRIN binding capacity are separated by means of using a linker or spacer group. Linker groups suitable for use in the present invention include, but are not limited to, modified or unmodified nucleotides, nucleosides, polymers, sugars, carbohydrates, polyalkylenes, such as polyethylene glycols and polypropylene glycols, polyalcohols, polypropylenes, mixtures of ethylene- and propylene glycols, polyalkylamines, polyamines such as polylysine and spermidine, polyesters such as poly(ethyl acrylate), polyphosphodiesters, aliphatic groups and alkylenes having a suitable length. In a preferred embodiment, the spacer group is polyethylene glycol. In an even more preferred embodiment, the polyethylene glycol is a PEG2000.

In a preferred embodiment, the nanoparticles of the invention comprise as the outer shell a single lipid layer and at least one molecule with EMMPRIN binding capacity, wherein the phospholipid molecules and the molecule with EMMPRIN binding capacity are connected through a polyethylene glycol residue.

In an even more preferred embodiment, said nanoparticles comprise as the outer shell a single lipid layer and at least one molecule with EMMPRIN binding capacity, wherein the phospholipid molecules and the molecule with EMMPRIN binding capacity are connected through a polyethylene glycol residue, and additionally, an agent for detection of said nanoparticles (a fluorophore and/or a paramagnetic/superparamagnetic core).

The agents for detecting the nanoparticles have to be suitable for viewing said nanoparticles. Illustrative examples of said agents include, but are not limited to, fluorescent, radioactive, paramagnetic and superparamagnetic agents. Said agents allow detecting the nanoparticles by means of magnetic resonance imaging, by fluorescence or by means of other techniques, according to the detection agent used. Illustrative examples of paramagnetic and superparamagnetic contrast agents that can be used in the invention include, but are not limited to, a derivative of gadolinium, iron oxide (FeO, $Fe_2O_3$, $Fe_3O_4$), platinum oxide (FePt), a derivative of gold and of bismuth. In a preferred embodiment, the paramagnetic core is FeO and is located in the core of the nanoparticle. In a preferred embodiment, if the nanoparticles are to be viewed by means of fluorescence, a fluorophore is added, inserted in the single phospholipid layer, such that the nanoparticles are visible by means of confocal microscopy or by fluorescence molecular tomography (FMT).

Fluorescent agents suitable for detecting the nanoparticles include, but are not limited to, ALEXA FLUOR (for example, ALEXA FLUOR 555 (a bright orange dye)), fluorescein, fluorescein isothiocyanate (FITC), OREGON GREEN (bright, green-fluorescent dye with; excitation ideally suited to the 488 nm laser line) rhodamine, TEXAS RED (bright red-fluorescent dye with excitation ideally suited to the 561 or 594 nm laser lines), tetrarhodamine isothiocyanate (TRITC), a CYDYE (for example, Cy2, Cy3, Cy5) and the like.

The nanoparticles of the invention can be used in preventing and/or treating a pathology in which EMMPRIN is overexpressed. Illustrative examples of said pathologies include, but are not limited to, any cardiac damage, cardiac damage arising after ischemia followed by reperfusion, heart infarct, adverse ventricular myocardial remodeling, several types of cancer (cervical cancer, prostate cancer, etc), ulcerated corneas, rheumatoid arthritis, etc. In a preferred embodiment, the nanoparticle is used for preventing and/or treating cardiac damage arising after ischemia followed by reperfusion.

If the nanoparticles are to be used for treating any pathology in which EMMPRIN is overexpressed, said nanoparticles comprise, in addition to the aforementioned elements, a compound of therapeutic interest modulating EMMPRIN activity. A person skilled in the art will understand that the agent/agents for detecting the nanoparticles are not necessary if the nanoparticles of the invention are used for therapeutic purposes, even though they can be used. The compound of therapeutic interest modulating EMMPRIN activity is preferably bound to the outer shell, although it can also be included in the central core of the nanoparticle. Illustrative examples of compounds of therapeutic interest comprised in the nanoparticle include, but are not limited to, an inhibitory peptide of EMMPRIN, such as AP-9 peptide, an anti-EMMPRIN antibody, a glycosylation modulator, a p53 activator, a PPAR-alpha antagonist, an siRNA, a cyclophilin ligand, a statin, an EMMPRIN-specific antisense oligonucleotide, an EMMPRIN-specific ribozyme, an EMMPRIN-specific aptamer and an EMMPRIN-specific Spiegelmer.

The nanoparticles of the invention can also be used for diagnosing a pathology in which EMMPRIN is overexpressed. Illustrative examples of said pathology include, but are not limited to, any cardiac damage, cardiac damage arising after ischemia followed by reperfusion, heart infarct, adverse ventricular myocardial remodeling, several types of cancer (cervical cancer, prostate cancer, etc), ulcerated corneas, rheumatoid arthritis, etc.

The following examples serve to illustrate the invention and must not be considered as limiting of the scope thereof.

EXAMPLES

Materials and Methods

Reagents

The cell culture reagents were from BD Biosciences (Spain), the fetal serum was from Bio Whittaker (Verviers, Belgium), the culture media and antibiotics were from Sigma (St. Louis, Mo., USA). The conjugated secondary antibodies were from GE Health Care (Spain). The protease inhibitor cocktail was from Roche (Spain). OPTIMEM medium and (a modification of Eagle's Minimum Essentials Media, buffered with HEPES and sodium bicarbonate, and supplemented with hypoxanthine, thymindine, sodium pyruvate, L-glutamine, trace elements, and growth factors) and LIPOFECTAMINE (cationic-lipid transfection reagent) were from GIBCO-BRL (BD), DETA-NO, SNAP and 1400W were from Alexis (Alexis Biochemicals, USA). Rp-8-Br-PET-cGMPs was from Biolog (Germany). The anti-MMP-9 and anti-MMP-2 antibodies were from BD Transduction Laboratories (BD Biosciences, Spain), whereas the anti-EMMPRIN antibody (rat-anti-mouse-EMMPRIN, OX114 clone) and control anti-EMMPRIN were from Serotec.

Mice

The iNOS gene knockout mice and their corresponding wild-type controls were purchased from The Jackson Laboratories (Bar Harbor, Me., USA), no differences in size or weight having been detected in same. All the animals were housed in stalls in the animal laboratory in isolated rooms free of microbiological contamination. This research was conducted according to the guides for the care and use of laboratory animals, published by the NIH (NIH Publication No. 85-23, revised 1996).

Cells

The HL1 cardiomyocyte cell line was donated by Dr. Antonio Bernad and cultured as described [Ruiz-Meana M et al. Cardiovascular research 2006; 71:715-724]. The RAW 274 murine macrophage line was cultured as described [Tarin C et al. Arteriosclerosis, thrombosis, and vascular biology 2009; 29:27-32].

Ischemia/reperfusion of the Coronary Artery

Ischemia was induced by means of the coronary artery ligation in the manner detailed below: twelve week old mice were anesthetized intraperitoneally by means of using ketamine/xylazine (100 mg/kg/10 mg/kg, respectively), intubated with a 1 mm steel tube, and ventilated (2 ml, 80 pulses/minute). After this process, the chest of the mice was opened between the second and third ribs, being kept open by means of the aid of a retractor for mice. The pericardium was then opened to subsequently temporarily ligate the left coronary artery in a region close to its branch by means of using a 6-0 silk suture and for a period of 30 minutes. Evidence of coronary occlusion was clearly shown by means of the discoloration of the left ventricle after the arterial ligation. After 30 minutes, the ligation is removed, the chest closed and the skin sutured. Additionally, a group of control animals (sham) were included in the assays, in which the same method was carried out with the exception of the coronary artery occlusion. To inhibit iNOS in vivo, the iNOS wild-type mice were injected in the tail vein with 2 mg/kg/day of the pharmacological inhibitor of iNOS, 1400W, 30 minutes before ischemia and 24 hours after ischemia/reperfusion. To neutralize EMMPRIN in vivo, a dose-response of administration of anti-EMMPRIN antibody or control IgG administered by intravenous injection was carried out. The effective dose of anti-EMMPRIN finally used was 250 micromol/L/kg, this being the dose at which a reduction of MMP-9 greater than 50% compared to the IgG control is observed. To evaluate the effect of anti-EMMPRIN on the ischemic process/reperfusion, the antibodies were administered intravenously for four days before the surgical procedure, after which time the infarct size, cardiac function and EMMPRIN and MMP-9 expression were evaluated.

Nitrite Assay

The nitrite concentration in samples was determined by means of a modification of the Griess assay as previously described [Zaragoza C et al. J Clin Invest 1997; 100:1760-1767]. In summary, 50 µl of sample and of nitrite standards were incubated at an equal volume with the Griess reagent (1% sulfanilamide, 0.1% naphthyl ethylenediamine and 2.5% $H_3PO_4$), for 10 minutes at room temperature, after which time the absorbance of each sample at a wavelength of 540 nm was evaluated in a microplate reader.

Echocardiography

The hearts of the mice were viewed by means of echocardiography over time using a high frequency micro-ultrasound equipment (Vevo 770, Visual Sonics, Toronto, Canada). To that end, the animals were anesthetized using isofluorane gas (1.5%), resulting in a heart rate of about 300 beats/minute. The mice were placed on a table coupled to a rail system, where the temperature at which the experiment is performed is further controlled and regulated. Their hair was removed to prevent artifact images, and to take images echocardiograph transmission gel is applied. Each animal in the experiment was used to obtain cardiac images of the B-mode parasternal short axis at a frequency of 30 MHz, which allowed obtaining M-mode images, for thus determining the end-diastolic diameter and volume of the left ventricle, the ejection fraction and the fractional shortening of the heart as a result of using the heart analysis software supplied in the equipment.

Histology and Immunohistochemistry

The heart of the animals was included in paraffin to subsequently obtain sections 4 microns thick as previously described [Tarin et al. mentioned ad supra]. The morphology of the heart was viewed by means of staining with hematoxylin and eosin, whereas collagen deposition was monitored by means of Masson's trichrome staining. For the immunohistochemical detection of EMMPRIN, MMP-9 and MMP-2, the samples were incubated with the corresponding primary antibodies and were viewed by means of confocal microscopy after incubation with the corresponding secondary antibodies conjugated with fluorescent reagents as previously described [Lopez-Rivera E et al. Proc Natl Acad Sci USA 2005; 102:3685-3690].

Gelatin Zymography

To evaluate the presence of MMPs in the cell lysates, the latter were resolved in 8.5-10% SDS-PAGE gels in the presence of 1 mg/ml of gelatin. The gels were incubated in renaturing buffer for 30 minutes (2.5% Triton X-100, (polyethylene glycol p-(1,1,3,3-tetramethylbutyl)-phenyl ether)) and subsequently incubated 16 hours in developing buffer (50 mM Tris-HCl (pH 7.5), 200 mM NaCl, 10 mM $CaCl_2$, 0.02% BRIJ 35) (polyethylene glycol dodecyl ether, Polyoxyethylene (23) lauryl ether)). Subsequently, the gels were incubated in the presence of Coomassie blue for 1 hour, and gelatinolytic activity was detected after incubation with rinsing solution (methanol:acetic acid:water, 50:10:4).

Cloning the Murine EMMPRIN Regulatory Region

To clone the mouse EMMPRIN promoter, commercial chromosome BAC CH29-603O5 (which contains part of murine chromosome 10), from CHORI (Children's Hospital Oakland Research Institute) was used as a template in PCR reactions with the following oligonucleotides:

```
                                         (SEQ ID NO: 36)
   Forward-5'-CGGGGTACCAGCACTCCATCCAAAGGCAGA-3'.

(SEQ ID NO: 37)
   Reverse-5'-GGAAGATCTGTCGCCTCGTCCAGGAGC-3'.
```

The resulting PCR fragment was cloned into the pGL3-Basic vector (Promega) at 5' position to the luciferase reporter gene (hereinafter referred to as pEMMPRIN-WT).

Mutagenesis of the EMMPRIN Promoter

For the purpose of carrying out the mutation of the specific promoter residues, pEMMPRIN was used as a template in PCR reactions to thus create serial deletions of the promoter as detailed:

p1000=pEMMPRIN-WT.

p500: plasmid containing the first 500 bps of the EMMPRIN promoter.

p250: plasmid containing the first 250 bps of the EMMPRIN promoter.

p1000-500: plasmid containing 500 distal bps of the EMMPRIN promoter.

p1000-750: plasmid containing 250 distal bps of the EMMPRIN promoter.

p875-750: plasmid containing the distal region of the EMMPRIN promoter comprised between bases 750 and 875 thereof.

A mutant was also generated for the E2F transcription factor binding site, located at position -790 of the EMMPRIN promoter, by means of using the site-directed mutagenesis kit from Stratagene, according to the instructions provided by the manufacturer, and using the following oligonucleotides (with the substitution mutations indicated in lower case letters) in PCR reactions. The oligonucleotides used to that end are the following:

```
   Forward:
                                         (SEQ ID NO: 38)
   5'-GGGGTTAGAAGCCTtCtCtACAGTGCACGACCTTCAAA-3'

Reverse:
                                         (SEQ ID NO: 39)
   5'-TTTGAAGGTCGTGCACTGTaGaGaAGGCTTCTAACCCC-3
```

Transient Transfection

The transient DNA transfection experiments were carried out by means of using the LIPOFECTAMINE (catatonic-lipid transfection reagent) 2000 reagent as previously described by the manufacturer. The luciferase content in the transfected cells was measured as previously described [Zaragoza C et al. Molecular pharmacology 2002; 62:927-935]. In summary, the cells were transiently transfected with 1 microgram of DNA and 10 µl of LIPOFECTAMINE (catatonic-lipid transfection reagent) 2000 in OPTIMEM culture medium (a modification of Eagle's Minimum Essential Media, buffered with HEPES and sodium bicarbonate, and supplemented with hypoxanthine, thymidine, sodium pyruvate, L-glutamine, trace elements, and growth factors) for 4 hours, after which time they were washed and incubated with fresh culture medium (MEM/10% FCS) for 16 hours. Furthermore, as a control, the cells were co-transfected with a plasmid containing the constitutively active promoter of cytomegalovirus fused with the R-Luciferase gene (Renilla), used as a control. Each sample was therefore evaluated for the content of both P-(firefly) and R-luciferase. P-luciferase is a substrate of the product of the reporter gene fixed to the promoter to be evaluated, and R-luciferase is a substrate of the gene product of the reporter gene of the co-transfected control plasmid. The results were normalized for R-Luciferase content.

mRNA Stability Assay

For this assay, cells were incubated in wells 2 mm in diameter and incubated in the presence of 10 µM of actinomycin D for 16 hours, after which time the cells were treated with diethylenetriamine-NO (DETA-NO) at different times. The RNA of the different experiment times was isolated and both for EMMPRIN and for GAPDH (as a control), their mRNAs were evaluated by means of quantitative real-time RT-PCR.

Statistical Analysis

The data is expressed as the mean value±the standard deviation of the sample. The cell culture assays were carried out 3 times, and each of the conditions was evaluated in duplicate or triplicate. In the case of animal experimentation, this was done in triplicate and the number of animals/replica was specified in the text. In the case of comparisons made with a common control, the comparisons were made by means of analysis of variance followed by the Dunnett modification of the Student's T-test. The level of statistical significance was defined as $p<0.05$. The error bars represent ±SD.

Example 1

Myocardial Infarct is Greater in iNOS Knockout Mice

The relevance of iNOS in cardioprotection was made evident by means of detection in coronary ischemia/reperfusion assays, by Western blot and by measuring NO levels in the hearts of wild-type (WT) mice (FIG. 1A), together with the observation of a drop in infarct sizes (FIG. 1B) and ejection fraction (FIG. 1C), when compared with the respective values obtained in the iNOS knockout animals. It should nevertheless be pointed out that the contribution of eNOS in the phenomenon cannot be cannot be excluded because other researchers have also been able to find significantly elevated eNOS levels as a result of infarct (de Waard M C et al. J Mol Cell Cardiol. 2010; 48:1041-9 and Yin C et al. Circ Res 2009; 104:572-575), and the NO levels detected in this research do not exclude the possible implication of eNOS in this context. The summary of parameters evaluated in these assays is shown in Table 1.

TABLE 1

Ultrasound parameters.

| | WT Control | WT IR | iNOS Control | iNOS IR |
|---|---|---|---|---|
| LVDS (mm) | 3.07 ± 0.3 | 3.50 ± 0.6 | 3.06 ± 0.28 | 4.10 ± 0.12 |
| LVDD (mm) | 4.17 ± 0.40 | 4.66 ± 0.11 | 4.24 ± 0.29 | 5.56 ± 0.49 |
| VS (ul) | 37.24 ± 3.07 | 53.00 ± 6.91 | 34.43 ± 6.94 | 59.78 ± 3.82 |
| VD (ul) | 57.43 ± 2.08 | 68.63 ± 4.81 | 59.45 ± 10.42 | 88.60 ± 15.28* |
| SV (ul) | 20.19 ± 4.01 | 15.63 ± 6.47 | 25.02 ± 3.62 | 28.82 ± 6.39* |
| EF (%) | 51.26 ± 3.70 | 42.49 ± 4.62 | 51.9 ± 4.15 | 30.53 ± 3.35* |
| FS (%) | 25.55 ± 2.21 | 20.66 ± 4.81 | 26.30 ± 1.98 | 14.94 ± 2.51* |
| Heart beat (bpm) | 326 ± 11.77 | 339 ± 23.33 | 355 ± 8.98 | 343 ± 60.80 |
| Weight (mg) | 120 ± 6.59 | 132 ± 6.12 | 110 ± 9.09 | 165 ± 19.25 |

LVDS: Left ventricle diameter, systolic.
LVDD: Left ventricle diameter, diastolic.
VS: Systolic volume.
DS: Diastolic volume.
SV: Systole/diastole volume differences.
EF: Ejection fraction.
FS: fractional shortening.
*p < 0.05 WT IR vs iNOS IR.

Example 2

EMMPRIN Expression is Induced in iNOS Knockout Mice

Figure 2:
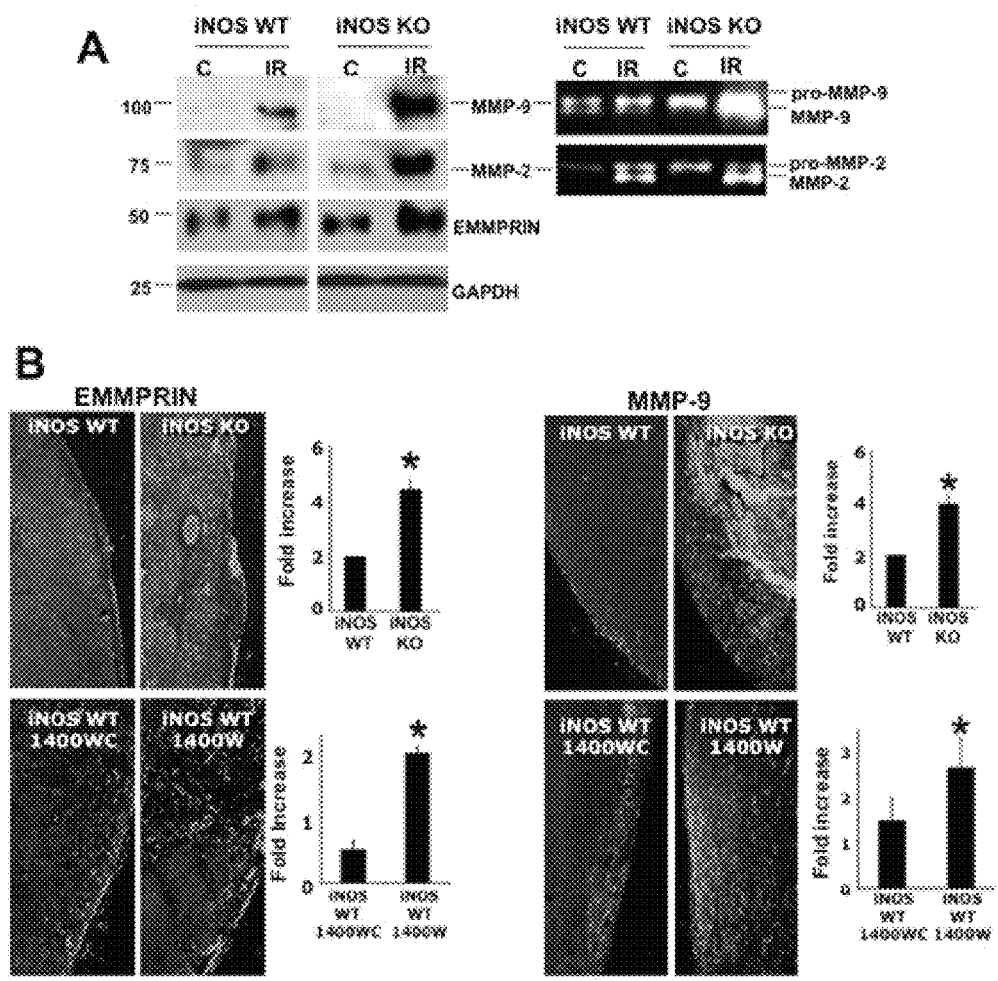
FIG. 2 describes that NO inhibits EMMPRIN and MMP-9 expression in ischemia/reperfusion. (A) left: After 30 minutes of ischemia and 24 hours of reperfusion, MMP-9, MMP-2, EMMPRIN, and GAPDH expression was evaluated by Western blot with specific antibodies. (A) right: Additionally, the presence of MMP-2 and MMP-9 was also evaluated by gelatin gel zymography. (B) EMMPRIN expression (panels on the left) in wild-type mice (iNOS WT), iNOS knockout mice (iNOS KO), and in mice in which the iNOS activity was pharmacologically inhibited with the compound 1400W (iNOS WT 1400W). A group of 1400W control animals was also evaluated (iNOS WT 1400WC). Densitometric analysis corresponding to the set of the signal obtained in each of the groups is represented on the right (n=10 mice in triplicate, mean±SD; *p<0.05 iNOS WT vs iNOS KO; # p<0.05 iNOS WT 1400WC vs iNOS WT 1400W). MMP-9 expression (panels on the right) in the same animals. (C) Effect of the pharmacological inhibition of iNOS on infarct sizes in wild-type mice (n=6 mice in triplicate. *p<0.05). (D) EMMPRIN expression in iNOS knockout mice: control operated animals (C), animals that suffered ischemia/reperfusion (I/R), and animals that suffered ischemia/reperfusion that were administered the NO donor sodium nitroprussiate (20 micrograms/kg/day) intravenously for 2 days prior to the procedure. To verify the presence of NO in the heart of the mice, confocal microscopy assays were carried out on heart sections of these animals with anti-3-nitro-tyrosine (n=6 mice).
Figure 2:
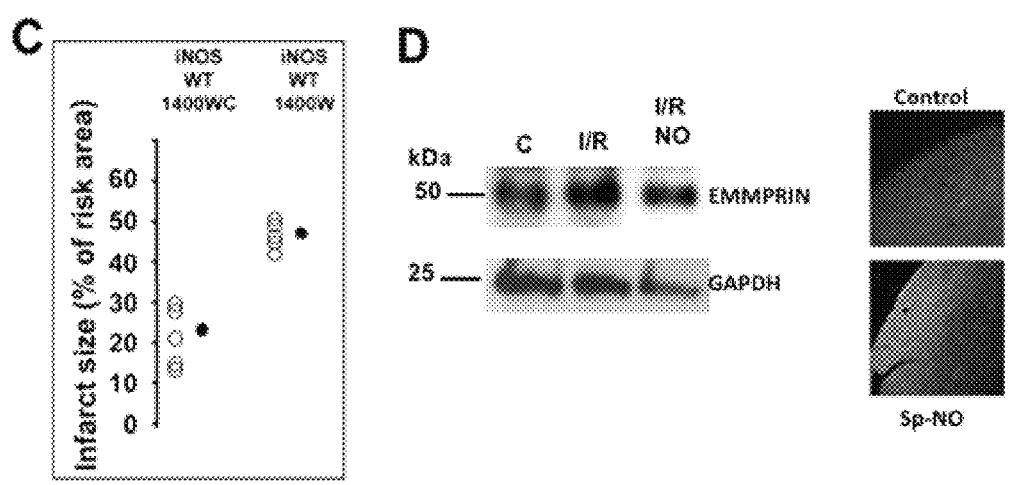

MMPs are significantly involved in the digestion of the cardiac extracellular matrix during myocardial infarct and their inductor, EMMPRIN, has been seen to be involved in a similar manner in MMP induction in heart cells [Schmidt R et al. Circulation 2006; 113:834-841]. For the purpose of evaluating the contribution of iNOS in this context, the authors of the present research detected that in iNOS knockout animals, EMMPRIN levels are significantly increased, and the myocardial infarct tends to further increase them with respect to the wild-phenotype animals, such process detected by means of Western blot. Both MMP-9 and MMP-2, two of the most representative MMPs present during infarct and EMMPRIN targets, are also overexpressed in iNOS knockout mice, detected both by means of Western blot (FIG. 2A left) and by means of zymography (FIG. 2A right).

Example 3 iNOS Inhibition Involves an Increase of Cardiac Damage and EMMPRIN Expression in iNOS Wild-type Mice To gain further knowledge about the effect of iNOS on the heart, the authors of the invention found that in iNOS wild-type mice, the administration of the pharmacological inhibitor of iNOS, 1400W, tends to significantly increase infarct size (FIG. 2C, box), together with the increase of EMMPRIN levels (FIG. 2B, lower panels on the left) and MMP-9 with respect to control mice (FIG. 2B, lower panels on the right, WT 1400WC vs WT 1400W), salvaging the same phenotype detected in the iNOS knockout animals. To evaluate this effect of NO to a greater extent, in iNOS knockout mice, the NO donor sodium nitroprussiate (20 micrograms/kg/day) was administered intravenously two days before ischemia/reperfusion (I/R NO), detecting a significant reduction in EMMPRIN levels compared to control mice (I/R) (FIG. 2D, left). Additionally, nitration was detected by means of using anti-3-Nitrotyrosine in sections isolated from those same animals, confirming that the exogenously supplied NO was present in the hearts of the animals treated during the time of the experiment (FIG. 2D, right). All these results suggest that EMMPRIN inhibition can be a signaling pathway used by NO in its cardioprotective effect.

Example 4 iNOS Regulates EMMPRIN Transcription in Cardiomyocytes

To investigate the capacity of NO to regulate EMMPRIN in murine hearts, EMMPRIN mRNA expression in wild-type mice and iNOS knockout mice was evaluated by means of quantitative RT-PCR, detecting how ischemia/reperfusion induces a significant increase of mRNA in the iNOS knockout mice when compared with that of wild-type mice (FIG. 3A). It could additionally be detected how mRNA levels were significantly reduced in cardiomyocytes in culture in the presence of the NO donor, DETA-NO (FIG. 3B), whereas in the RAW macrophage cell line, NO did not induce a significant effect on EMMPRIN gene expression (FIG. 3C), thus suggesting a role for NO in the EMMPRIN transcription in cardiomyocytes. To further investigate the effect of iNOS on EMMPRIN expression, de novo RNA synthesis in the cardiomyocyte cell line was inhibited by means of using actinomycin D. In this context, EMMPRIN mRNA levels were evaluated by means of quantitative RT-PCR over time, thus being capable of detecting a significant reduction in mRNA stability by NO (FIG. 3D, left). In contrast, as occurs with mRNA expression, NO had no effect whatsoever on macrophage stability (FIG. 3D, right).

In view of the obtained results, it all indicates the relationship between NO and EMMPRIN in mouse cardiomyocytes, suggesting that the reduction detected in the mRNA levels of this protein could be one of the molecular mechanisms carried out by NO that contribute to its cardioprotective effect.

Example 5

NO Induces Transcriptional Repression of the EMMPRIN Promoter in Cardiomyocytes

To analyze in depth the repressive effect of NO on the EMMPRIN transcription, the first 1000 bps of the regulatory region of the EMMPRIN gene, fused to the luciferase reporter gene (pEMMPRIN-WT), were cloned. By means of transient transfection of cardiomyocytes with this construct, the negative effect that NO has on gene transcription in a dose-dependent manner (FIG. 4A) and cGMP-dependent manner (FIG. 4B) could be detected because the soluble analogue of cGMP, 8-Br-cGMP, caused the same effect as the NO donor used in the transfection assays. To explore this effect in greater detail, how the pharmacological inhibition of the cGMP-dependent kinase, PKG, by means of adding the inhibitor Rp-8-Br-PET-cGMPS (PET) caused a significant increase of EMMPRIN promoter activity (PET, FIG. 4C) could be detected, whereas in combination with NO, PET inhibitor was capable of partially restoring the negative effect of NO on promoter activity (PET+NO, FIG. 4C). Additionally, overexpression of the dominant positive construct of cGMP-dependent kinase alpha isoform, PKG1-alpha (fG1AC) [14] in cardiomyocytes transfected with the EMMPRIN promoter (pEMMPRIN-WT) involved a significant reduction of promoter transcriptional activity (FIG. 4C, fG1AC).

The effect of NO was additionally verified by means of incubating transfected cells in the presence of two additional NO donors such as S-Nitroso-N-acetyl-D,L-penicillamine (SNAP) and (Z)-1-N-[3-aminopropyl]-N-[4-(3-aminopropylammonio)butyral]-amino}-diazen-1-ium-1,2-diolate (Spermine-NONOate), obtaining results similar to those generated with DETA-NO.

Figure 4:
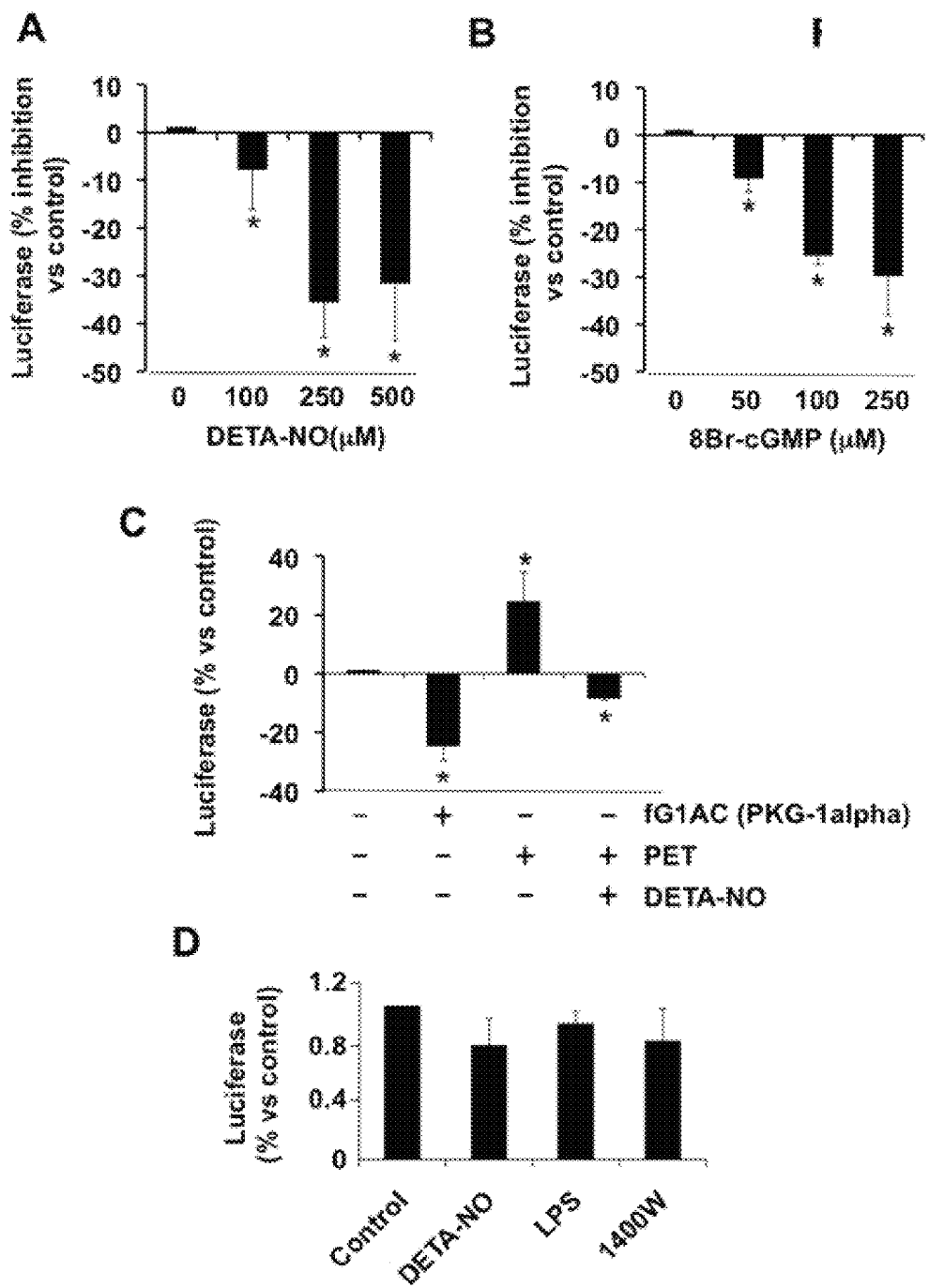
FIG. 4 shows that NO transcriptionally regulates EMMPRIN in cardiomyocytes through the cGMP/PKG pathway. (A) Dose response of the NO donor DETA-NO on EMMPRIN promoter transcriptional activity in cardiomyocytes transiently transfected with pEMMPRIN-WT (n=10, mean±SD *p<0.05 vs 0). (B) Dose response of the cGMP analogue, 8-Br-cGMP, on EMMPRIN promoter transcriptional activity in cardiomyocytes transiently transfected with pEMMPRIN-WT (n=10, mean±SD *p<0.05 vs 0). (C) Effect of PKG on EMMPRIN promoter transcriptional activity in cardiomyocytes transiently transfected with pEMMPRIN-WT, and co-transfected with the dominant positive construct of PKG-1 alpha (fG1AC), or treated with the pharmacological inhibitor of PKG PET, in the presence or absence of 100 µM DETA-NO (n=3, mean±SD *p<0.05 vs transfected while dormant (−). (D) Effect of the exogenous addition of 100 µM DETA-NO, endogenous NO production with LPS, and the pharmacological inhibition of iNOS (100 µM 1400W) on EMMPRIN promoter transcriptional activity in RAW 247.6 cells that were transiently transfected with pEMMPRIN-WT (n=3 mean, ±SD).

Finally, both the exogenous administration of NO and induction of endogenous production by means of incubation with LPS, did not induce any significant differences with regard to EMMPRIN promoter activity in murine macrophages (FIG. 4D). Taking into account the obtained results, said results allow suggesting the capacity of NO to regulate EMMPRIN transcription through the cGMP/PKG pathway in cardiomyocytes. To completely characterize the specific location of the effect of NO on the EMMPRIN promoter, transient cardiomyocyte transfection assays were conducted with constructs containing serial deletions of the promoter. With it, the authors of the invention were capable of determining that the repressive effect of NO is located in the promoter region comprised between bases −875 and −750 (FIG. 5A), and additionally, by means of a detailed analysis of this region they could determine the existence of different binding sites for transcription factors, including an E2F factor binding site, whose inhibitory effect on transcription for different genes had previously been characterized [Agromayor M et al. Mol Cell Biol 2006; 26:4448-4461].

To explore if NO exerts its repressive effect through E2F, point deletion of the binding domain in the EMMPRIN promoter was carried out, detecting that in cells transfected with this construct, NO lacked any repressive effect on promoter activity, thus indicating that it is most likely at least one of the mechanisms of action of NO on transcriptional activity of EMMPRIN in cardiomyocytes (FIG. 5B).

Example 6

Figure 6:
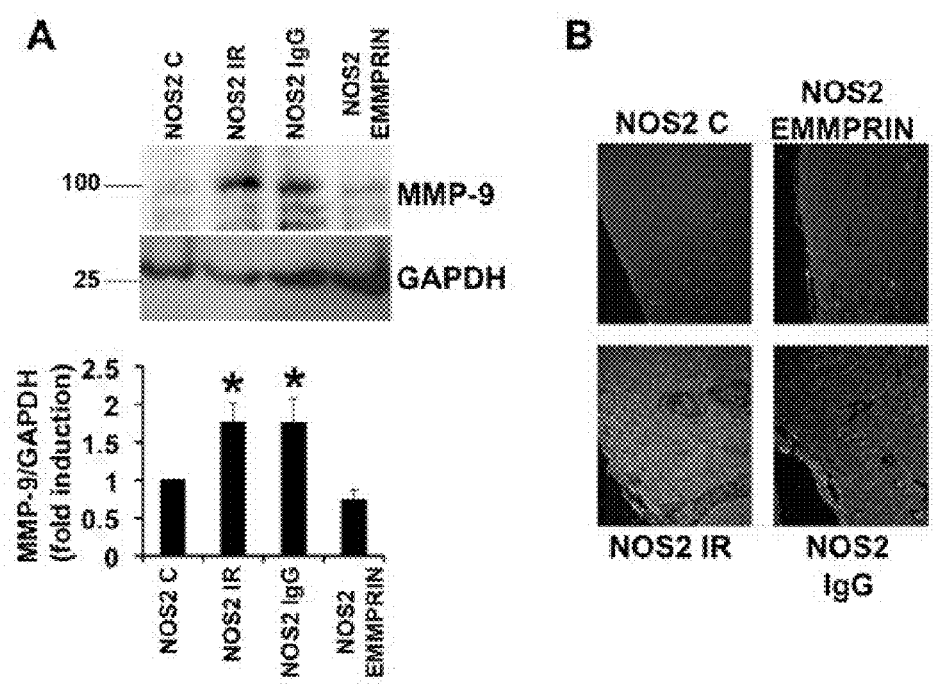
FIG. 6 shows that the administration of anti-EMMPRIN antibodies partially restores cardiac function and inhibits MMP-9 expression. (A) MMP-9 detection by means of Western blot in control mice (NOS2 C), in mice that have suffered ischemia/reperfusion (NOS2 IR), in mice that were intravenously administered IgG for 4 days and that have subsequently suffered ischemia/reperfusion (NOS2 IgG) and in mice that were intravenously administered anti-EMMPRIN for 4 days and that have subsequently suffered ischemia/reperfusion (NOS2 EMMPRIN) (n=6 per group, mean±SD. *p<0.05 vs NOS2C). (B) EMMPRIN detection in the same mice by means of confocal microscopy. (C) Ejection fraction values in iNOS knockout mice (NOS2) and in wild-type mice (WT) (n=6 per group, mean±SD. *p<0.05 NOS2 IR vs NOS2-EMMPRIN and NOS2 IgG vs NOS2 EMMPRIN)
Figure 6:
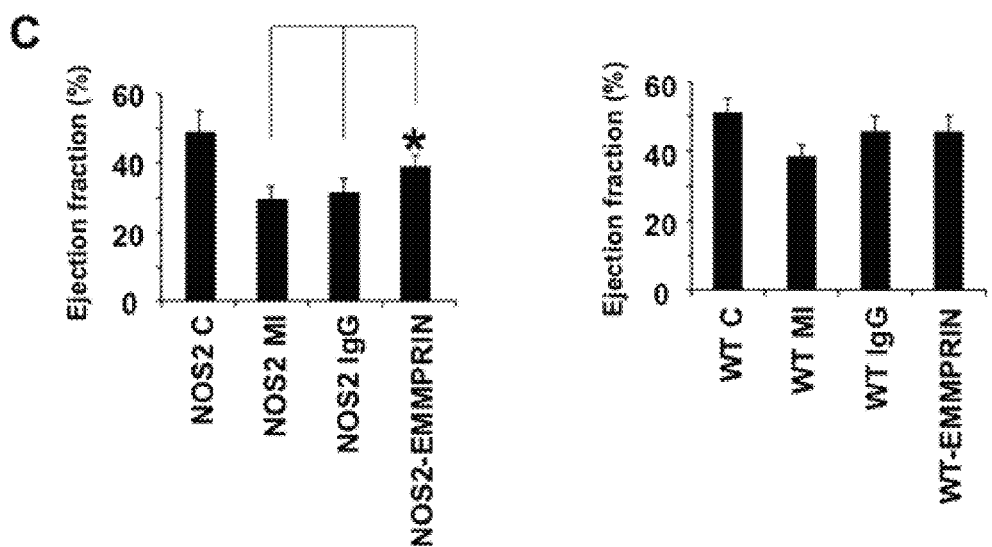

EMMPRIN Inhibition in iNOS Knockout Mice Restores the Wild-type Phenotype in Ischemia/reperfusion To evaluate the potential effect of EMMPRIN regulation in vivo, anti-EMMPRIN antibodies (generated with an epitope corresponding to the N-terminal end in the extracellular region) was administered, or murine IgG1 was administered as a control. Four days after the intravenous administration of the antibody, coronary ischemia/reperfusion was induced in the wild-type and iNOS knockout mice, detecting significant inhibition in MMP-9 expression after the administration of the EMMPRIN-specific antibody, compared to the mice injected with IgG1 or injected with no immunoglobulin (FIG. 6A). Interestingly, it could in turn be observed how the endogenous EMMPRIN levels were also reduced as a result of the administration of the antibody that specifically recognizes EMMPRIN (FIG. 6B). Concerning cardiac function, it could be ascertained that the administration of anti-EMMPRIN involved a significant increase of the ejection fraction values in the hearts of iNOS knockout animals compared with those obtained in control mice and in mice injected with IgG1 (FIG. 6C, left). Concerning wild-type mice, anti-EMMPRIN antibodies were also positive for improving cardiac contraction (FIG. 6C, right), indicating that EMMPRIN could be a target of NO during the cardioprotection process.

Example 7

EMMPRIN Inhibition in Mice by Administration of AP-9 Peptide

Figure 9:
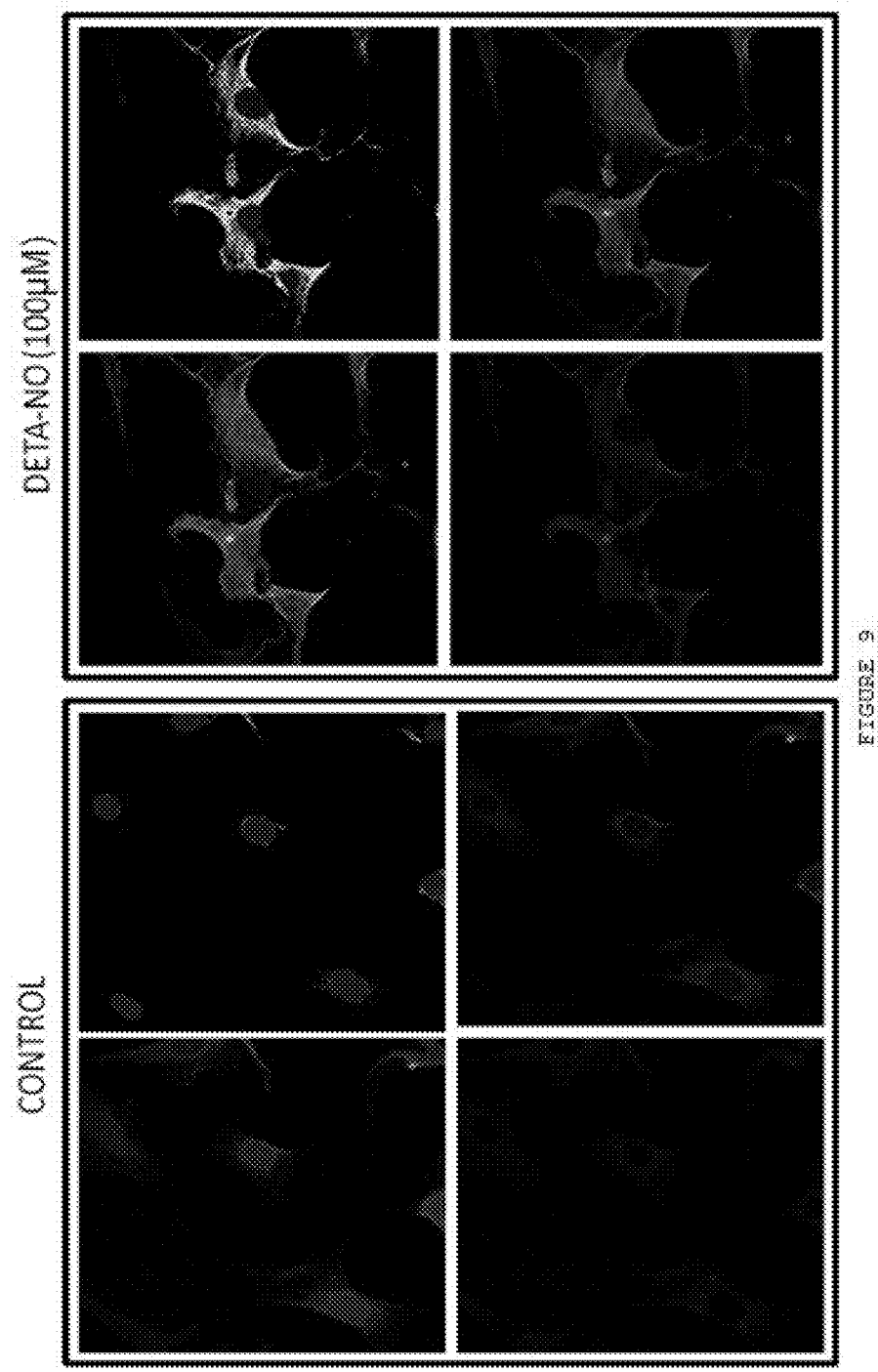
FIG. 9 shows that the AP-9 peptide binds to EMMPRIN in mouse aortic endothelial cells (MAEC). The MAEC cells were incubated overnight with the nitric oxide donor (DETA-NO) (100 µM) to induce EMMPRIN expression (right panel). The MAEC cells without DETA-NO were used as a control (left panel). The MAEC cells were fixed with 4% PFA and incubated with 0.08 mg/ml of AP-9 peptide. EMMPRIN expression was detected using an anti-EMMPRIN antibody (1:1000), observing that both signals co-localize (right panel, top right square). The cores were stained with DAPI.

MAEC cells (mouse aortic endothelial cells) were used for the in vitro assays. Said cells were incubated overnight with the nitric oxide donor (DETA-NO) (100 μM) to induce EMMPRIN expression. The MAEC cells without DETA-NO were used as a control. The MAEC cells were fixed with 4% PFA and incubated with 0.08 mg/ml of AP-9 peptide. EMMPRIN expression was subsequently detected using an anti-EMMPRIN antibody (1:1000). FIG. 9 shows that AP-9 peptide signal and the EMMPRIN signal are co-localized, so it is concluded that AP-9 peptide binds specifically to EMMPRIN.

Figure 10:
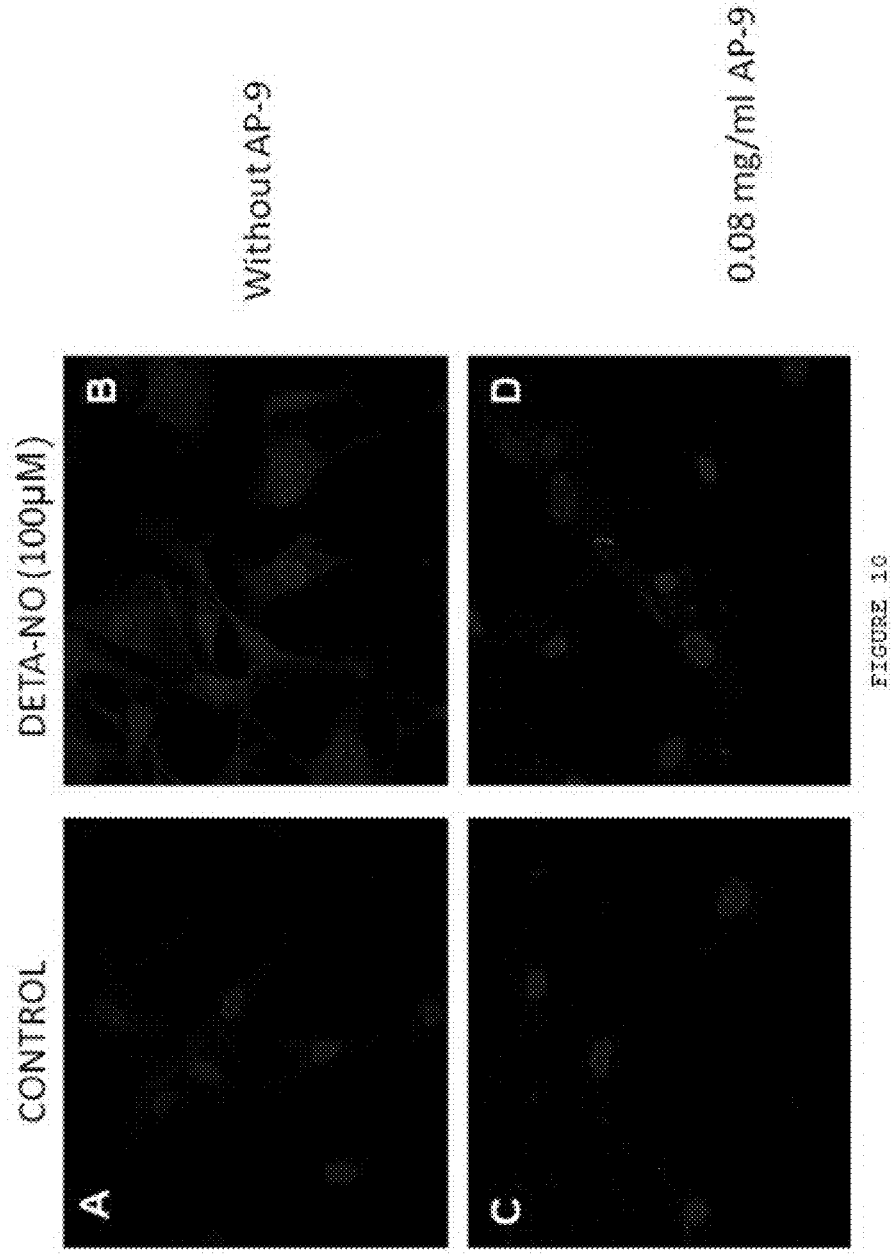
FIG. 10 shows that the AP-9 peptide blocks EMMPRIN-induced MMP-9 expression. MAEC cells were incubated with 100 µM of DETA-NO to induce EMMPRIN expression (B, D). MAEC cells without DETA-NO were used as a control (A, C). After 3 hours of treatment with DETA-NO, the MAEC cells were incubated overnight with AP-9 peptide (0.08 mg/ml) (C, D) or with PBS (A, B). The MAEC cells were fixed with 4% PFA, and MMP-9 expression was detected using an anti-MMP-9 antibody (1:1000). The MAEC cells incubated with AP-9 peptide showed inhibition of the EMMPRIN-induced MMP-9 expression. The cores were stained with DAPI.

Likewise, to ascertain if AP-9 peptide inhibited EMMPRIN-induced MMP-9 expression, MAEC cells were incubated with 100 μM of DETA-NO to induce EMMPRIN expression. After 3 hours of treatment with DETA-NO, the MAEC cells were incubated overnight with AP-9 peptide (0.08 mg/ml) or with PBS as a control without peptide. MAEC cells without DETA-NO were used as a control. Finally, the MAEC cells were fixed with 4% PFA and MMP-9 expression was detected using an anti-MMP-9 antibody (1:1000). As can be seen in FIG. 10, the MAEC cells incubated with AP-9 peptide showed the inhibition of EMMPRIN-induced MMP-9 expression.

For the in vivo assays, AP-9 peptide synthesis was carried out in two different ways: in one way labeled with a fluorochrome for detection by means of immunohistochemical techniques and by means of the non-invasive approach of fluorescence tomography, and in a second way with biotinylated AP-9 for the purpose of being able to be fixed and perform pull down assays to evaluate the existence of molecules interacting with EMMPRIN on which to act with a possible effect of modulating the activity thereof.

Pilot AP-9 peptide administration assays were initially carried out to evaluate the effect of AP-9 peptide and to thus determine the stability and half-life of AP-9 in the animals over time. To that end, AP-9 was intravenously administered at the following concentrations: 10 ng/kg, 100 ng/kg 1 μg/kg, 10 μg/kg, 100 μg/kg, 1 mg/kg, 10 mg/kg.

Each group consisted of 9 animals, which were used in groups of 3 for the non-invasive fluorescent viewing of the peptide by means of tomography on a daily basis, and each day one group of 3 animals was sacrificed to conduct an immunohistofluorescent analysis of the hearts isolated from the animals. According to the experimental design, a total of 189 mice were necessary for the test since the assays were conducted in triplicate.

Once the optimal administration concentration was determined, the optimal dose of AP-9 was intravenously injected into five groups of mice that have suffered ischemia/reperfusion:

Group 1. Administration of AP-9, 1 hour before ischemia.
Group 2. Administration of AP-9, during the ischemic process.
Group 3. Administration of AP-9, 1 hour after the ischemia, during the reperfusion period.
Group 4. Administration of scramble AP-9 (peptide with the same amino acids as AP-9 with a random sequence) to mice that suffered ischemia/reperfusion.
Group 5. Animals that suffered ischemia/reperfusion.

Progression of the damage was evaluated by means of ultrasound in all the mice, determining cardiac parameters on a daily basis for three consecutive days. Likewise, the animals were also object of fluorescence tomography analysis to view the presence of AP-9 in hearts, at the end of which the animals were sacrificed to conduct histological and immunohistochemical analysis for the purpose of evaluating the expression of proteolytic enzymes MMP-2 and MMP-9.

Example 8

EMMPRIN Inhibition by Means of Using Nanoparticles Containing AP-9 Peptide
I. Materials and Methods
The following protocol was followed to conjugate the AP-9 peptide to the nanoparticles:

1. The following were dissolved in a mixture of chloroform:methanol (6:1):
   10 mg of 20 nm iron oxide nanocrystals in chloroform,
   47.5 mg (95%) of DSPC-PEG2000
   2.5 mg (5%) of Maleimide PEG
   0.5 mg (1%) of NIR664-DSPE dissolved in chloroform:methanol
2. The mixture was added dropwise to 4-10 ml of deionized water at 80° C., subsequently allowing it to cool.
3. To activate the peptide, AP-9 peptide was incubated with the deacetylation solution (0.5 M hydroxylamine, 1 M HEPES, 32 mM EDTA, pH 7.0) for 1 hour. The molar ratio of Maleimide PEG and AP-9 peptide was 1:1; to that end 137 µl of the peptide, 363 µl of PBS and 50 µl of deacetylation solution were added.
4. Activated AP-9 peptide was added to the mixture with the iron oxide nanoparticles. Said mixture was incubated overnight at 4° C.
5. It was centrifuged for 1 hour at 8000 rpm, removing the supernatant. PBS was added to wash the pellet, centrifuging again for 1 hour at 8000 rpm and repeating the process twice to purify the nanoparticles.

Figure 7:
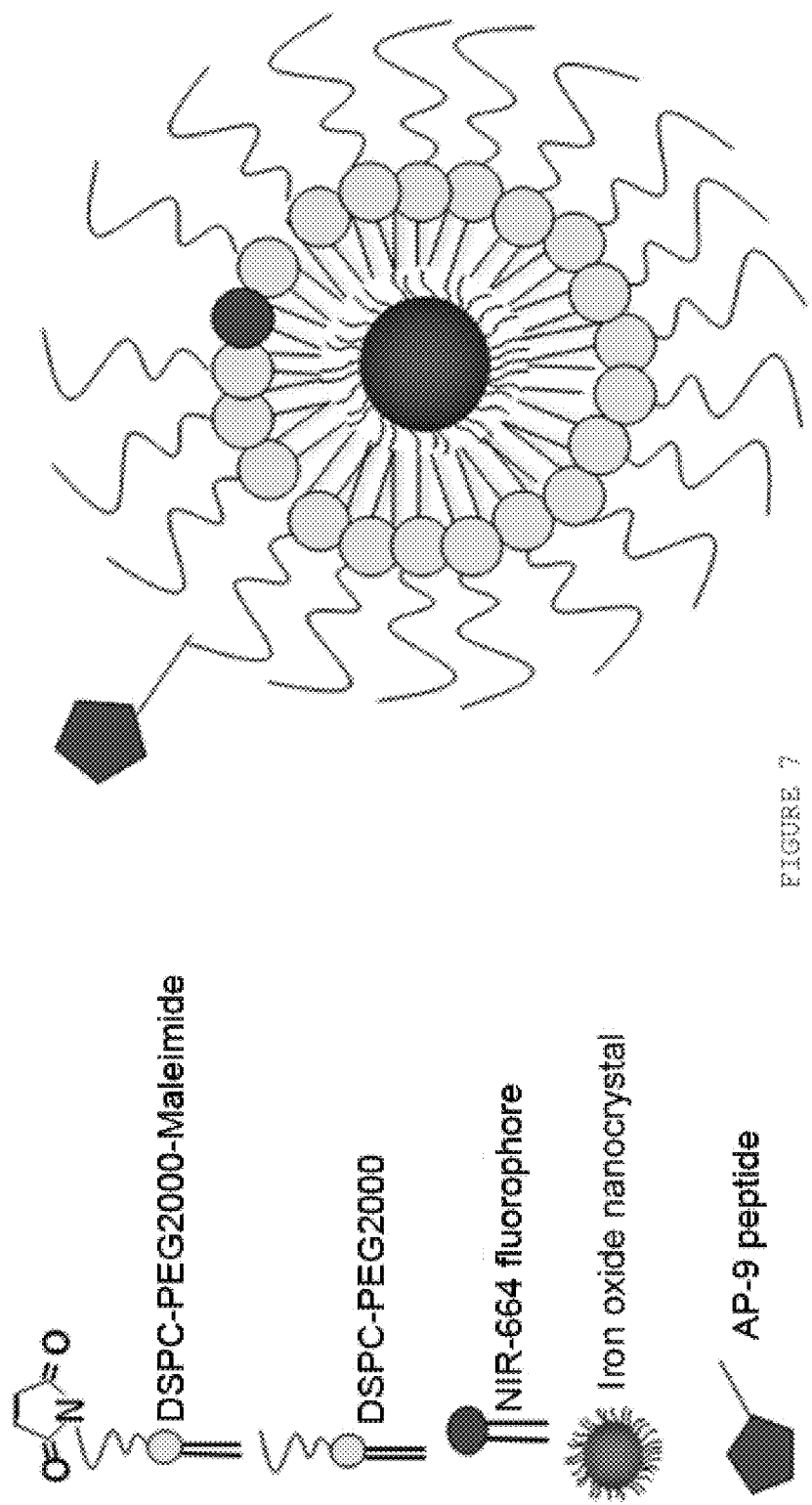
FIG. 7 represents the nanoparticles loaded with AP-9 peptide. The nanoparticles were synthesized with phospholipids-PEG, fluorescent lipids and an iron oxide nanocrystal core, the AP-9 peptide was subsequently bound to the surface.
Figure 8:
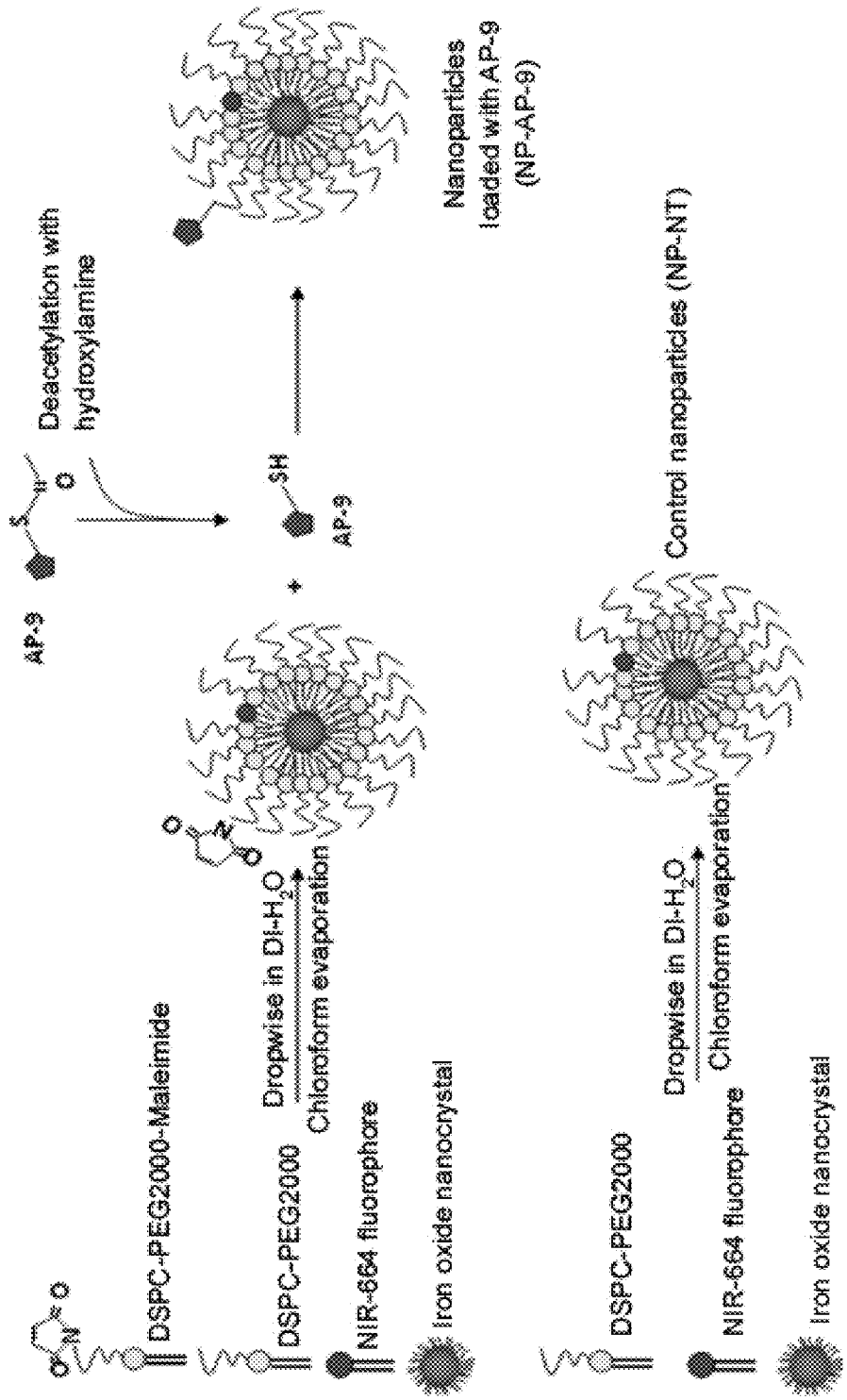
FIG. 8 shows a nanoparticle synthesis diagram. The nanoparticles were synthesized with lipids-PEG, fluorescent lipids and an iron oxide nanocrystal as the central core. The AP-9 peptide was then bound to the surface. Nanoparticles without the AP-9 peptide bound thereto were used as a control.

The synthesized nanoparticles consist of the following structure, which can be observed in FIG. 7 and FIG. 8:

1. Central iron oxide core, visible by magnetic resonance imaging (MRI).
2. Single lipid layer with a fluorochrome (confocal microscopy, fluorescence tomography, FMT)
3. AP-9 peptide (EMMPRIN target).

II. Results
The main object of using the nanoparticles was to be able to provide a vehiculization, multimodal viewing and effector tool with respect to EMMPRIN activity and the possible regression of the damage in the myocardium.

Figure 11:
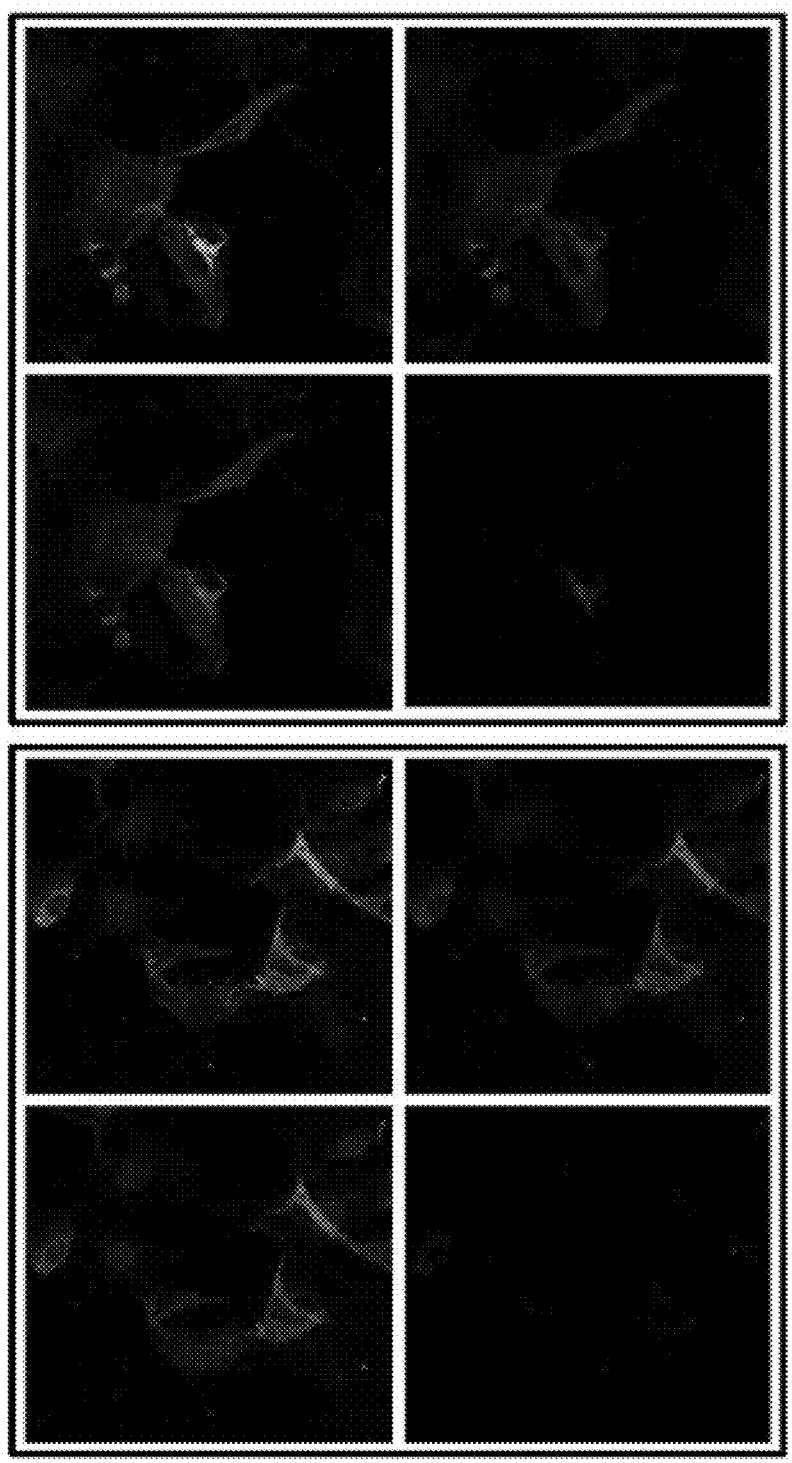
FIG. 11 shows internalization of the AP-9 nanoparticles by MAEC cells. The MAEC cells were incubated overnight with the AP-9 nanoparticles (NP-AP-9) (20 µg/ml) (right panel) or with non-loaded nanoparticles (NP-NT) (left panel). The MAEC cells were fixed, and EMMPRIN expression was detected using an anti-EMMPRIN antibody. Co-localization between the NP-AP-9 signal and the EMMPRIN signal was found in MAEC cells treated with NP-AP-9 (right panel), but this co-localization was not found in the control nanoparticles. The cores were stained with DAPI.
Figure 12:
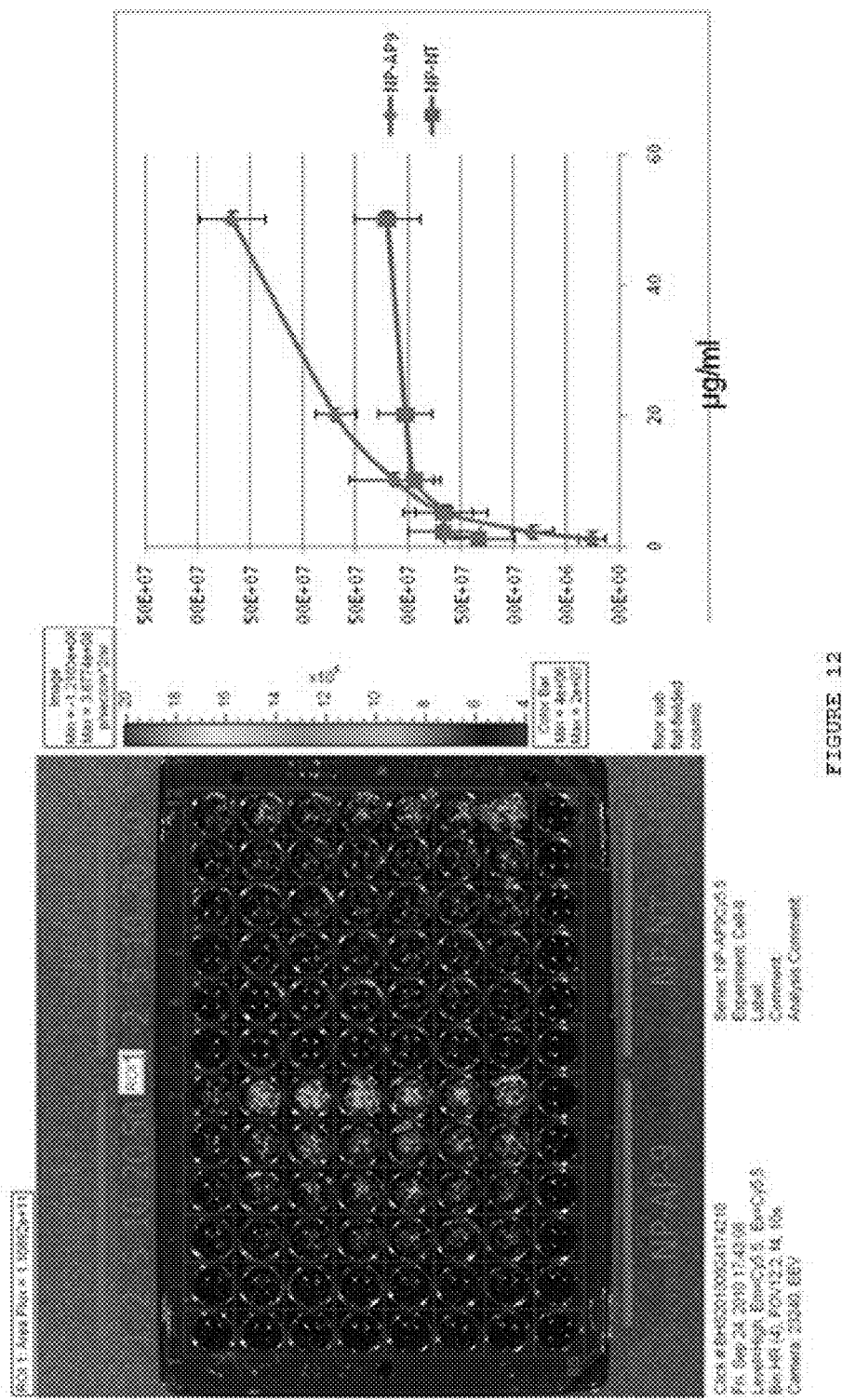
FIG. 12 shows that the MAEC cells internalized the AP-9 nanoparticles in a dose-dependent manner. The MAEC cells were cultured in a black 96-well plate and incubated overnight with different concentrations of nanoparticles loaded with AP-9 (NP-AP9) or nanoparticles without AP-9 (NP-NT). Fluorescence was measured using an IVIS imaging system. The graph on the right represents the intensity of the fluorescence signal of the image on the left.

Nanoparticles containing AP-9 have therapeutic value, because EMMPRIN is inhibited and tissue damage due to proteolytic enzyme activation is reduced. As shown in FIG. 11, it is observed that the nanoparticles could be internalized into mouse aortic endothelial cells and that they are viable inside the cell, AP-9 peptide binding to EMMPRIN. Likewise, it is observed in FIG. 12 that said internalization occurs in a dose-dependent manner, observing how the fluorescent signal increases as the peptide concentration increases.

On the other hand, as in the previous case where AP-9 peptide was administered, pilot nanoparticle administration assays were initially performed to thus determine nanoparticle stability and half-life in the animals over time. To that end, the AP-9-conjugated nanoparticle (N-AP-9) was intravenously administered at the following concentrations: 10 µg/kg, 100 µg/kg, 1 mg/kg and 10 mg/kg.

Each group consisted of 9 animals, which were used in groups of 3 for the non-invasive fluorescent viewing by means of fluorescence tomography (FMT) and magnetic resonance imaging (MRI) on a daily basis, and each day a group of 3 animals was sacrificed to conduct an immunohistofluorescent analysis of the hearts isolated from the animals to validate the non-invasive imaging results. According to this experimental design, a total of 96 mice were necessary for the test since the assays were conducted in triplicate.

Once the optimal parameters of minimum concentration at which the best view of AP-9 could be obtained by means of fluorescence and MRI were obtained, NP-AP-9 was intravenously administered in the following 5 groups of animals:

Group 1. Administration of NP-AP-9, 1 hour before ischemia.
Group 2. Administration of NP-AP-9, during the ischemic process.
Group 3. Administration of NP-AP-9, 1 hour after ischemia, during the reperfusion period.
Group 4. Administration of scramble NP-AP-9 (nanoparticle with a conjugated peptide having the same composition but a different order of amino acids with respect to AP-9) to mice that suffered ischemia/reperfusion.
Group 5. Animals that suffered ischemia/reperfusion.

As a result of such technology, a tool was obtained that allowed the following:

1—Non-invasively viewing the infarcted heart by means of resonance/fluorescence.
2—NP-AP-9-EMMPRIN binding to be able to view EMMPRIN by means of non-invasive molecular imaging.
3—Inducing cardiac damage regression by inhibiting the effect of metalloproteinase type proteolytic enzymes.

As in previous cases, progression of the damage was evaluated by means of ultrasound in all the mice, determining cardiac parameters on a daily basis for three consecutive days. Likewise, the animals were also object of fluorescence tomography analysis (FMT) and MRI to view the presence of EMMPRIN in hearts, at the end of which the animals were sacrificed to conduct histological and immunohistochemical analysis for the purpose of evaluating the expression of proteolytic enzymes MMP-2 and MMP-9 and thus calculating, together with the ultrasound data, the possible regression induced by the nanoparticle.

The invention claimed is:

1. A nanoparticle comprising on its surface a molecule with Extracellular Matrix Metalloproteinase Inducer (EMMPRIN) binding capacity, wherein the molecule with EMMPRIN binding capacity is the inhibitory AP-9 peptide, the sequence of which is SEQ ID NO: 3.

2. The nanoparticle according to claim 1 comprising an outer phospholipid shell.

3. The nanoparticle according to claim 2, wherein the phospholipid shell is modified with polyethylene glycol.

4. The nanoparticle according to claim 2, wherein the phospholipid shell is modified with a fluorophore.

5. The nanoparticle according to claim 1, wherein the core of the nanoparticle comprises iron oxide.

6. A method for preventing and/or treating cardiac damage arising after ischemia followed by reperfusion comprising administering to a patient in need of such treatment an inhibitory AP-9 peptide, the sequence of which is SEQ ID NO: 3.

7. A method for diagnosing a pathology in which Extracellular Matrix Metalloproteinase Inducer (EMMPRIN) is overexpressed in a subject comprising contacting a sample from said subject with the nanoparticle according to claim 1 and detecting binding of the nanoparticle to said sample, wherein the pathology in which EMMPRIN is overexpressed is myocardial damage.

8. A nanoparticle comprising on its surface an Extracellular Matrix Metalloproteinase Inducer (EMMPRIN) binding molecule and internally an inhibitory AP-9 peptide, the sequence of which is SEQ ID NO: 3, wherein the EMMPRIN binding molecule is an anti-EMMPRIN antibody or the AP-9 peptide, the sequence of which is SEQ ID NO:3.

9. The nanoparticle according to claim 8 comprising an outer phospholipid shell.

10. The nanoparticle according to claim 9 wherein the phospholipid shell is modified with polyethylene glycol.

11. A method for preventing and/or treating cardiac damage arising after ischemia followed by reperfusion comprising administering to a patient in need of such treatment the nanoparticle according to claim 8.

* * * * *

SEQUENCE LISTING

<160> NUMBER OF SEQ ID NOS: 39

<210> SEQ ID NO 1
<211> LENGTH: 269
<212> TYPE: PRT
<213> ORGANISM: Homo sapiens

<400> SEQUENCE: 1

Met Ala Ala Ala Leu Phe Val Leu Leu Gly Phe Ala Leu Leu Gly Thr
1               5                   10                  15

His Gly Ala Ser Gly Ala Ala Gly Thr Val Phe Thr Thr Val Glu Asp
            20                  25                  30

Leu Gly Ser Lys Ile Leu Leu Thr Cys Ser Leu Asn Asp Ser Ala Thr
        35                  40                  45

Glu Val Thr Gly His Arg Trp Leu Lys Gly Gly Val Val Leu Lys Glu
    50                  55                  60

Asp Ala Leu Pro Gly Gln Lys Thr Glu Phe Lys Val Asp Ser Asp Asp
65                  70                  75                  80

Gln Trp Gly Glu Tyr Ser Cys Val Phe Leu Pro Glu Pro Met Gly Thr
                85                  90                  95

Ala Asn Ile Gln Leu His Gly Pro Pro Arg Val Lys Ala Val Lys Ser
            100                 105                 110

Ser Glu His Ile Asn Glu Gly Glu Thr Ala Met Leu Val Cys Lys Ser
        115                 120                 125

Glu Ser Val Pro Pro Val Thr Asp Trp Ala Trp Tyr Lys Ile Thr Asp
    130                 135                 140

Ser Glu Asp Lys Ala Leu Met Asn Gly Ser Glu Ser Arg Phe Phe Val
145                 150                 155                 160

Ser Ser Ser Gln Gly Arg Ser Glu Leu His Ile Glu Asn Leu Asn Met
                165                 170                 175

Glu Ala Asp Pro Gly Gln Tyr Arg Cys Asn Gly Thr Ser Ser Lys Gly
            180                 185                 190

Ser Asp Gln Ala Ile Ile Thr Leu Arg Val Arg Ser His Leu Ala Ala
        195                 200                 205

Leu Trp Pro Phe Leu Gly Ile Val Ala Glu Val Leu Val Leu Val Thr
    210                 215                 220

Ile Ile Phe Ile Tyr Glu Lys Arg Arg Lys Pro Glu Asp Val Leu Asp
225                 230                 235                 240

Asp Asp Asp Ala Gly Ser Ala Pro Leu Lys Ser Ser Gly Gln His Gln
                245                 250                 255

Asn Asp Lys Gly Lys Asn Val Arg Gln Arg Asn Ser Ser
            260                 265

<210> SEQ ID NO 2
<211> LENGTH: 119
<212> TYPE: PRT
<213> ORGANISM: Artificial Sequence
<220> FEATURE:
<223> OTHER INFORMATION: Synthetic Construct

<400> SEQUENCE: 2

Ala Gly Phe Val Gln Ala Pro Leu Ser Gln Gln Arg Trp Val Gly Gly
1               5                   10                  15

Ser Val Glu Leu His Cys Glu Ala Val Gly Ser Pro Val Pro Glu Ile
            20                  25                  30

Gln Trp Trp Phe Glu Gly Gln Gly Pro Asn Asp Thr Cys Ser Gln Leu
        35                  40                  45

```
Trp Asp Gly Ala Arg Leu Asp Arg Val His Ile His Ala Thr Tyr His
     50                  55                  60

Gln His Ala Ala Ser Thr Ile Ser Ile Asp Thr Leu Val Glu Glu Asp
 65                  70                  75                  80

Thr Gly Thr Tyr Glu Cys Arg Ala Ser Asn Asp Pro Asp Arg Asn His
                 85                  90                  95

Leu Thr Arg Ala Pro Arg Val Lys Trp Val Arg Ala Gln Ala Val Val
            100                 105                 110

Leu Val Leu Glu Pro Gly Thr
        115

<210> SEQ ID NO 3
<211> LENGTH: 12
<212> TYPE: PRT
<213> ORGANISM: Artificial Sequence
<220> FEATURE:
<223> OTHER INFORMATION: Synthetic Construct

<400> SEQUENCE: 3

Tyr Lys Leu Pro Gly His His His His Tyr Arg Pro
 1               5                  10

<210> SEQ ID NO 4
<211> LENGTH: 29
<212> TYPE: DNA
<213> ORGANISM: Artificial Sequence
<220> FEATURE:
<223> OTHER INFORMATION: Synthetic Construct

<400> SEQUENCE: 4
aagaccttgg ctccaagata ccctgtctc                              29

<210> SEQ ID NO 5
<211> LENGTH: 29
<212> TYPE: DNA
<213> ORGANISM: Artificial Sequence
<220> FEATURE:
<223> OTHER INFORMATION: Synthetic Construct

<400> SEQUENCE: 5
aagtatcttg gagccaaggt ccctgtctc                              29

<210> SEQ ID NO 6
<211> LENGTH: 20
<212> TYPE: DNA
<213> ORGANISM: Artificial Sequence
<220> FEATURE:
<223> OTHER INFORMATION: Synthetic Construct

<400> SEQUENCE: 6
guucuucgug aguuccuctt                                        20

<210> SEQ ID NO 7
<211> LENGTH: 20
<212> TYPE: DNA
<213> ORGANISM: Artificial Sequence
<220> FEATURE:
<223> OTHER INFORMATION: Synthetic Construct

<400> SEQUENCE: 7
ttcaagaagc acucaaggag                                        20

<210> SEQ ID NO 8
```

```
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
gguucuucgu gaguuccuct t                                          21

<210> SEQ ID NO 9
<211> LENGTH: 21
<212> TYPE: DNA
<213> ORGANISM: Artificial Sequence
<220> FEATURE:
<223> OTHER INFORMATION: Synthetic Construct

<400> SEQUENCE: 9
gaggaacuca cgaagaacct g                                          21

<210> SEQ ID NO 10
<211> LENGTH: 19
<212> TYPE: RNA
<213> ORGANISM: Artificial Sequence
<220> FEATURE:
<223> OTHER INFORMATION: Synthetic Construct

<400> SEQUENCE: 10
guaggaccgg cgaggaaua                                             19

<210> SEQ ID NO 11
<211> LENGTH: 19
<212> TYPE: RNA
<213> ORGANISM: Artificial Sequence
<220> FEATURE:
<223> OTHER INFORMATION: Synthetic Construct

<400> SEQUENCE: 11
gaccuuggcu ccaagauac                                             19

<210> SEQ ID NO 12
<211> LENGTH: 19
<212> TYPE: RNA
<213> ORGANISM: Artificial Sequence
<220> FEATURE:
<223> OTHER INFORMATION: Synthetic Construct

<400> SEQUENCE: 12
gucgucagaa cacaucaac                                             19

<210> SEQ ID NO 13
<211> LENGTH: 19
<212> TYPE: RNA
<213> ORGANISM: Artificial Sequence
<220> FEATURE:
<223> OTHER INFORMATION: Synthetic Construct

<400> SEQUENCE: 13
gaucacugac ucugaggac                                             19

<210> SEQ ID NO 14
<211> LENGTH: 19
<212> TYPE: RNA
<213> ORGANISM: Artificial Sequence
<220> FEATURE:
<223> OTHER INFORMATION: Synthetic Construct

<400> SEQUENCE: 14
```

-continued ugacaaaggc aagaacguc                                          19

<210> SEQ ID NO 15
<211> LENGTH: 19
<212> TYPE: RNA
<213> ORGANISM: Artificial Sequence
<220> FEATURE:
<223> OTHER INFORMATION: Synthetic Construct

<400> SEQUENCE: 15
guuggguuuu cuccauuca                                          19

<210> SEQ ID NO 16
<211> LENGTH: 21
<212> TYPE: DNA
<213> ORGANISM: Artificial Sequence
<220> FEATURE:
<223> OTHER INFORMATION: Synthetic Construct

<400> SEQUENCE: 16
gggaaugcuc caaacgacat t                                       21

<210> SEQ ID NO 17
<211> LENGTH: 21
<212> TYPE: DNA
<213> ORGANISM: Artificial Sequence
<220> FEATURE:
<223> OTHER INFORMATION: Synthetic Construct

<400> SEQUENCE: 17
ugucguuugg agcauuccct t                                       21

<210> SEQ ID NO 18
<211> LENGTH: 21
<212> TYPE: DNA
<213> ORGANISM: Artificial Sequence
<220> FEATURE:
<223> OTHER INFORMATION: Synthetic Construct

<400> SEQUENCE: 18
ggaucaaggu cggaaagaat t                                       21

<210> SEQ ID NO 19
<211> LENGTH: 21
<212> TYPE: DNA
<213> ORGANISM: Artificial Sequence
<220> FEATURE:
<223> OTHER INFORMATION: Synthetic Construct

<400> SEQUENCE: 19
uuuuuuccga ccuugaucct t                                       21

<210> SEQ ID NO 20
<211> LENGTH: 21
<212> TYPE: DNA
<213> ORGANISM: Artificial Sequence
<220> FEATURE:
<223> OTHER INFORMATION: Synthetic Construct

<400> SEQUENCE: 20
gagccuuacc uuacagaaat t                                       21

<210> SEQ ID NO 21
<211> LENGTH: 21
<212> TYPE: DNA

```
<213> ORGANISM: Artificial Sequence
<220> FEATURE:
<223> OTHER INFORMATION: Synthetic Construct

<400> SEQUENCE: 21
uuucuguaag guaaggcuct t                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Construct

<400> SEQUENCE: 22
gcagugaccc agaccgcaat t                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Construct

<400> SEQUENCE: 23
uugcggucug ggucacugct t                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Construct

<400> SEQUENCE: 24
gagctacaca ttgagaacct g                                              21

<210> SEQ ID NO 25
<211> LENGTH: 33
<212> TYPE: DNA
<213> ORGANISM: Artificial Sequence
<220> FEATURE:
<223> OTHER INFORMATION: Synthetic Construct

<400> SEQUENCE: 25
tgattcctag gctagctaca acgatcctcg ccg                                 33

<210> SEQ ID NO 26
<211> LENGTH: 33
<212> TYPE: DNA
<213> ORGANISM: Artificial Sequence
<220> FEATURE:
<223> OTHER INFORMATION: Synthetic Construct

<400> SEQUENCE: 26
cagcgcgaag gctagctaca acgacccagc agc                                 33

<210> SEQ ID NO 27
<211> LENGTH: 33
<212> TYPE: DNA
<213> ORGANISM: Artificial Sequence
<220> FEATURE:
<223> OTHER INFORMATION: Synthetic Construct

<400> SEQUENCE: 27
tgaggagtag gctagctaca acgacttgga gcc                                 33
```

<210> SEQ ID NO 28
<211> LENGTH: 33
<212> TYPE: DNA
<213> ORGANISM: Artificial Sequence
<220> FEATURE:
<223> OTHER INFORMATION: Synthetic Construct

<400> SEQUENCE: 28
tgatcaccag gctagctaca acgagccccc ctt                33

<210> SEQ ID NO 29
<211> LENGTH: 33
<212> TYPE: DNA
<213> ORGANISM: Artificial Sequence
<220> FEATURE:
<223> OTHER INFORMATION: Synthetic Construct

<400> SEQUENCE: 29
ggagctggag gctagctaca acgagttggc cgt                33

<210> SEQ ID NO 30
<211> LENGTH: 33
<212> TYPE: DNA
<213> ORGANISM: Artificial Sequence
<220> FEATURE:
<223> OTHER INFORMATION: Synthetic Construct

<400> SEQUENCE: 30
cctcgttgag gctagctaca acgagtgttc tga                33

<210> SEQ ID NO 31
<211> LENGTH: 33
<212> TYPE: DNA
<213> ORGANISM: Artificial Sequence
<220> FEATURE:
<223> OTHER INFORMATION: Synthetic Construct

<400> SEQUENCE: 31
agtcagtgag gctagctaca acgacttgta cca                33

<210> SEQ ID NO 32
<211> LENGTH: 33
<212> TYPE: DNA
<213> ORGANISM: Artificial Sequence
<220> FEATURE:
<223> OTHER INFORMATION: Synthetic Construct

<400> SEQUENCE: 32
cggcctccag gctagctaca acgagttcag gtt                33

<210> SEQ ID NO 33
<211> LENGTH: 33
<212> TYPE: DNA
<213> ORGANISM: Artificial Sequence
<220> FEATURE:
<223> OTHER INFORMATION: Synthetic Construct

<400> SEQUENCE: 33
ggagcgtgag gctagctaca acgagatggc ctg                33

<210> SEQ ID NO 34
<211> LENGTH: 33
<212> TYPE: DNA
<213> ORGANISM: Artificial Sequence
<220> FEATURE:

```
<223> OTHER INFORMATION: Synthetic Construct

<400> SEQUENCE: 34
gcaccagcag gctagctaca acgactcagc cac                              33

<210> SEQ ID NO 35
<211> LENGTH: 33
<212> TYPE: DNA
<213> ORGANISM: Artificial Sequence
<220> FEATURE:
<223> OTHER INFORMATION: Synthetic Construct

<400> SEQUENCE: 35
cctttgtcag gctagctaca acgatctggt gct                              33

<210> SEQ ID NO 36
<211> LENGTH: 30
<212> TYPE: DNA
<213> ORGANISM: Artificial Sequence
<220> FEATURE:
<223> OTHER INFORMATION: Synthetic Construct

<400> SEQUENCE: 36
cggggtacca gcactccatc caaaggcaga                                  30

<210> SEQ ID NO 37
<211> LENGTH: 27
<212> TYPE: DNA
<213> ORGANISM: Artificial Sequence
<220> FEATURE:
<223> OTHER INFORMATION: Synthetic Construct

<400> SEQUENCE: 37
ggaagatctg tcgcctcgtc caggagc                                     27

<210> SEQ ID NO 38
<211> LENGTH: 38
<212> TYPE: DNA
<213> ORGANISM: Artificial Sequence
<220> FEATURE:
<223> OTHER INFORMATION: Synthetic Construct

<400> SEQUENCE: 38
ggggttagaa gccttctcta cagtgcacga ccttcaaa                         38

<210> SEQ ID NO 39
<211> LENGTH: 38
<212> TYPE: DNA
<213> ORGANISM: Artificial Sequence
<220> FEATURE:
<223> OTHER INFORMATION: Synthetic Construct

<400> SEQUENCE: 39
tttgaaggtc gtgcactgta gagaaggctt ctaacccc                         38
```